US008690794B1

(12) United States Patent
Gallardo

(10) Patent No.: US 8,690,794 B1
(45) Date of Patent: Apr. 8, 2014

(54) SYSTEM AND METHOD FOR COLLECTION OF HUMAN BODILY WASTE SAMPLES

(71) Applicant: Core Medical Products, LLC, McAllen, TX (US)

(72) Inventor: Geoffrey Gallardo, Camarillo, CA (US)

(73) Assignee: Core Medical Products, LLC, McAllen, TX (US)

( * ) Notice: Subject to any disclaimer, the term of this patent is extended or adjusted under 35 U.S.C. 154(b) by 0 days.

(21) Appl. No.: 13/830,954

(22) Filed: Mar. 14, 2013

(51) Int. Cl.
A61B 10/00 (2006.01)

(52) U.S. Cl.
USPC .......................................... 600/562

(58) Field of Classification Search
USPC ............ 600/573, 562; 422/58, 68.1; 220/737; 248/311.2, 312; 73/61.41
See application file for complete search history.

(56) References Cited

U.S. PATENT DOCUMENTS

| | | | |
|---|---|---|---|
| 3,571,817 A | 3/1971 | Gosnell | |
| 4,466,445 A | 8/1984 | Abrams | |
| 5,730,149 A | 3/1998 | Nakayama et al. | |
| 5,913,832 A | 6/1999 | Sagalovich et al. | |
| 6,212,698 B1 | 4/2001 | Stingley et al. | |
| 6,358,477 B1 | 3/2002 | Webb et al. | |
| 6,775,852 B1 | 8/2004 | Alvarez et al. | |
| 7,011,634 B2 | 3/2006 | Paasch et al. | |
| 8,091,848 B1 | 1/2012 | Reed | |
| 2004/0267158 A1* | 12/2004 | Paasch et al. | 600/573 |
| 2008/0112847 A1* | 5/2008 | Chen | 422/58 |
| 2009/0076413 A1 | 3/2009 | Robles | |

FOREIGN PATENT DOCUMENTS

JP      2009-288127 A      12/2009

* cited by examiner

Primary Examiner — Brian Szmal
(74) Attorney, Agent, or Firm — Knobbe Martens Olson & Bear, LLP

(57) ABSTRACT

According to some embodiments, systems and methods for the collection of human waste samples are provided. The systems include a collection bowl, defined as a generally bowl-shaped part extending downward from a toilet seat-shaped rim and having a collection port at the bottom of the collection bowl, a sample cup releasably coupleable to the collection port having a collection volume in communication with the collection bowl, a collection basket lined with a screen to collect solid and particulate matter, and a sample spatula to manipulate solid waste. The method generally includes: placing at least the collection bowl coupled with the sample cup on the porcelain rim of a toilet, replacing the toilet seat down over the collection bowl to hold the collection bowl in place, sitting on the toilet, voiding either liquid or solid waste into the collection bowl, ensuring waste enters the sample cup, emptying excess waste from the collection bowl, de-coupling the sample cup from the collection bowl, capping the sample cup, and discarding the collection bowl.

20 Claims, 31 Drawing Sheets

SYSTEM AND METHOD FOR COLLECTION OF HUMAN BODILY WASTE SAMPLES

BACKGROUND

1. Field

The present invention relates to devices, systems and methods for collecting samples of human bodily waste. More specifically, the present invention relates to devices, systems and methods for collecting samples of urine, kidney stones, or stools using a toilet bowl insert.

2. Description of the Related Art

There are many situations in which samples of human wastes are required for testing. The current state of the art requires a patient to hold a relatively small sample cup closely proximate to the urethral opening and voiding a comparatively small volume into the cup. Such a manual into-the-cup urination collection method can prove to be quite difficult for many individuals, including, but not limited to: those with impaired manual dexterity who are unable to grasp a sample cup appropriately; those with weakness who may be unable to grasp a sample cup appropriately; those with nervous disorders causing manual shaking; those who are morbidly obese and unable to access the anatomical regions necessary to take a urine sample; those who are pregnant and have difficulty with movement; those with bladder control issues or incontinence who may not be able to appropriately start and stop a stream of urine; those who are elderly; those who are very young; those who are partially or totally physically incapacitated; and those who are partially or totally mentally incapacitated. As has been illustrated and will be understood, the collection of waste samples can be a particular trying, embarrassing, and degrading experience for many people.

Accordingly, there is a need for improved devices, systems and methods for collecting human bodily waste samples.

SUMMARY

In accordance with one embodiment, a sample collection system for urine, stool or kidney stone samples is provided. The system comprises a monolithic sample collection body and a sample cup. The monolithic sample collection body has a circumferential rim and a collection bowl that extends downwardly from the rim and is configured for placement on a toilet such that the rim is positioned on the toilet rim and the collection bowl extends into a portion of the toilet. Additionally, the collection body includes a collector port extending from the bottom of the collection bowl. The sample cup is releasably coupleable to the collector port of the sample collection body such that a collection volume of the sample cup is in communication with the collection bowl. The sample collection body is configured to receive a urine, stool or kidney stone sample from a user and direct it to the collection volume in the sample cup via the collection bowl.

In accordance with another embodiment, a sample collection system for urine, stool, or kidney stone samples is provided. The system comprises a semi-rigid sample collection body and a sample cup. The semi-rigid sample collection body has a circumferential rim and a collection bowl extending downward from the rim, and is configured for placement on a toilet. During use, the rim of the collection bowl is held between the toilet rim and the toilet seat, such that the collection bowl extends into the toilet bowl. The collection body has one or more drainage troughs, and a collector port which is in communication with the one or more drainage troughs. The sample cup is configured to be releasably coupleable to the collector port such that a collection volume of the sample cup is in communication with the collection bowl. The sample collection body is configured to receive a urine, stool or kidney stone sample from a user and direct it to the collection volume in the sample cup via the collection bowl while only touching the rim of the toilet.

In accordance with another embodiment, a kit for use with an interior of a toilet bowl to collect a urine, stool, or kidney stone sample is provided. The kit includes a monolithic sample collection body, a sample cup, and a collection basket. The sample collection body has a circumferential rim and a curved collection bowl extending down from the rim to a collector port which extends from the collection body at an acute angle relative to a plane defined by the rim. The sample cup is releasably coupleable to the collector port and a collection volume of the sample cup is in communication with the collection bowl. The collection basket is removably insertable into the sample cup and includes a basket with a screen configured to allow a liquid to flow through while substantially disallowing passage of solid material therethrough.

DETAILED DESCRIPTION

Figure 1:
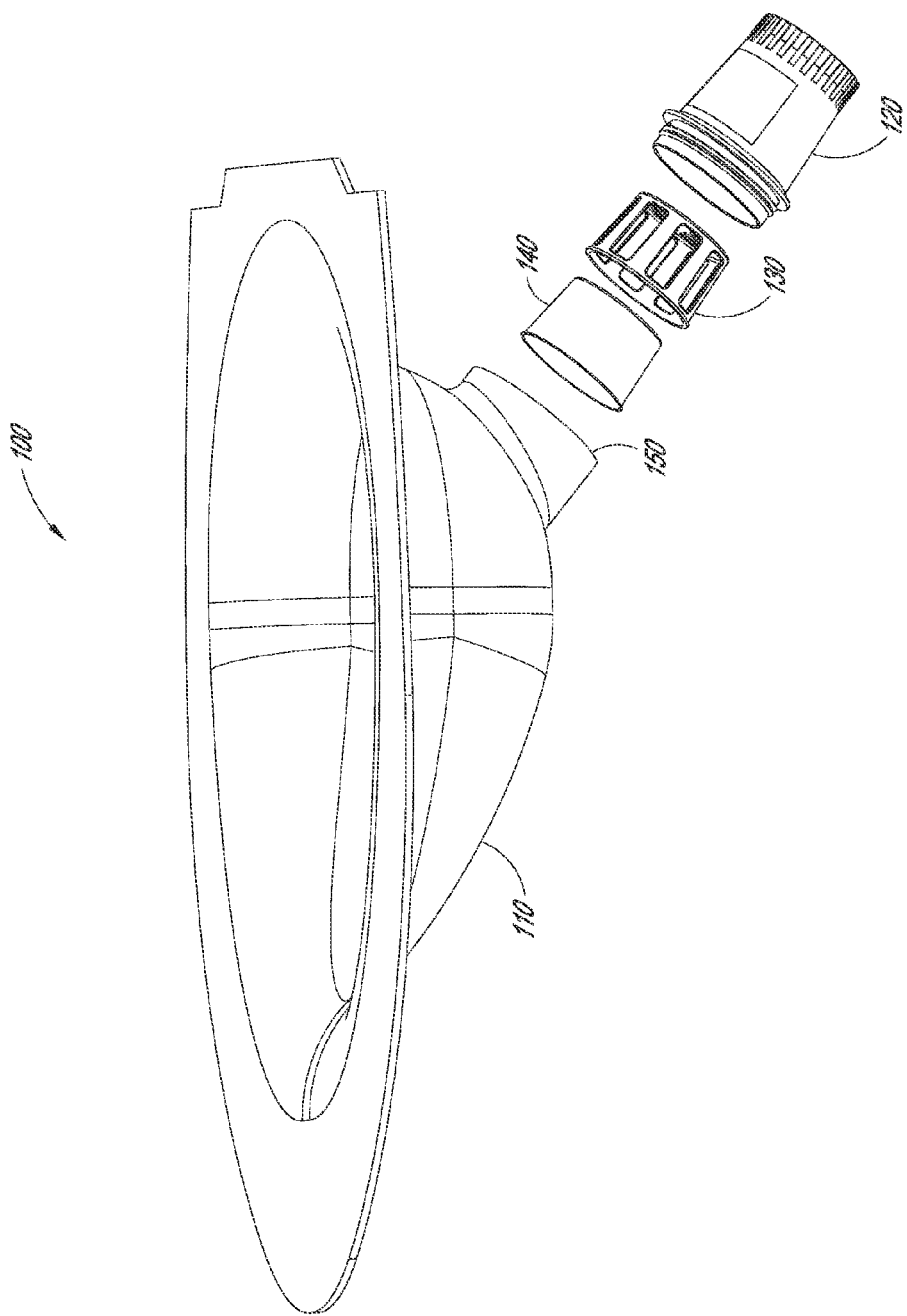
FIG. 1 is a top-biased, side exploded schematic view of one embodiment of a system for collecting samples of human waste products.

FIG. 1 illustrates an exploded view of one embodiment of a sample collection device 100. The embodiment of a sample collection device 100 can include a collection bowl 110, a sample cup 120, a collection basket 130, a screen 140, and a collector port 150.

In operation according to one embodiment, the screen 140 can be inserted into the collection basket 130 to form a collection basket 130 with a screen 140 lining. The collection basket 130 can then be inserted into the sample cup 120 which has a coupling mechanism at its upper end. In further operation, the combination of the screen 140, collection basket 130, and sample cup 120 can be coupled to the collection bowl 110 via the collector port 150 which also has a coupling mechanism. In another embodiment, the collection basket 130 and screen 140 can be a single piece (e.g., monolithic). In still another embodiment, the basket 130 and screen 140 can be excluded and the sample cup 120 can be coupled to the collector port 150.

Figure 2:
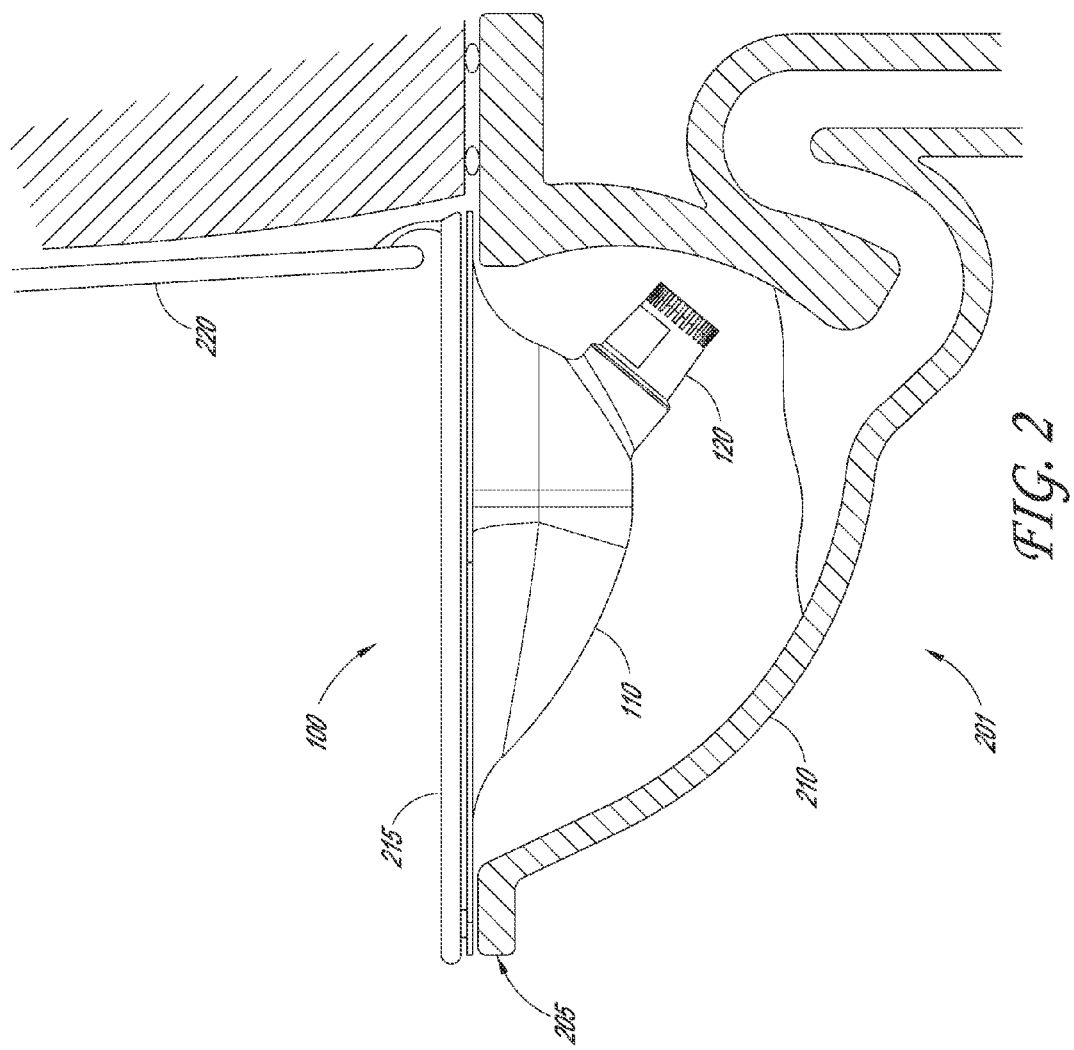
FIG. 2 is a side schematic view of one embodiment of a system for collecting samples of human waste products for use with a toilet.

FIG. 2 illustrates an embodiment of the sample collection device 100 in use on a toilet. In operation according to one embodiment, the sample collection device 100 can be assembled as described with reference to FIG. 1: the screen 140 can be inserted into the collection basket 130 which can be inserted into the sample cup 120 which can be removably coupled to the collector port 150 of the collection bowl 110. In further operation, a user may lift the toilet seat ring 215 of a toilet 201 and place the sample collection device 100 onto the toilet rim 205 of the toilet 201. In one embodiment, the sample collection device 100 can be dimensioned such that the sample collection device 100 substantially only touches (e.g., only touches) the toilet 201 at the toilet rim 205 of the toilet 201. By extension, in one embodiment the sample collection device 100 can be dimensioned such that the sample collection device 100 never touches the toilet bowl 210 of the toilet 201, as shown in FIG. 2. In still another embodiment, the sample collection device 100 can be dimensioned such that at least the sample cup assembly of the sample collection device 100 does not touch the toilet 201 (or water in the toilet). In further operation in accordance with one embodiment, the user can then put the toilet seat ring 215 of the toilet 201 down over the sample collection device 100. In another embodiment, the user can leave the toilet seat 215 up and simply sit down onto the sample collection device 100. The user may then void waste, including liquid wastes (i.e., urine), solid wastes (i.e., fecal matter), or kidney stones (e.g., via their urine) into the sample collection device 100. In continued operation, the waste matter can then be collected by the sample cup 120 of the sample collection device 100. After all desired waste has been collected, the toilet seat ring 215 of the toilet 201 can be lifted (i.e., where the toilet seat 215 was previously lowered over the rim of the sample collection device 100), the sample collection device 100 can be lifted out of the toilet bowl (e.g., pivoted about the distal edge of the sample collection device 100 to transfer any overflow of sample from the collection bowl 110 into the toilet bowl), and the sample cup 120 can be cleanly de-coupled from the collector port 150 of the collection bowl 110 and capped and labeled. In final operation, the collection bowl 110 can be disposed of (e.g., placed in a waste bin).

In some embodiments, the sample collection device 100 can be sized to seat into and be used with a standard sized elongated toilet bowl 210. In the United States, elongated toilet bowls 210 are used in substantially all, if not all, commercial, non-residential applications. The dimensions of an elongated toilet bowl 210 are standardized across the United States toilet 201 industry. In other embodiments, the sample collection device 100 can be sized to seat into and be used with a standard sized round toilet bowl 210. In the United States, round toilet bowls 210 are used primarily in residential applications. The dimensions of a round toilet bowl 210 are also standardized across the United States toilet 201 industry. In yet other embodiments, it will be understood that the sample collection device 100 can be sized to seat into and be used with a toilet bowl 210 of any size. Ultimately, the sample collection device 100 can easily be adapted by one of ordinary skill in the art to seat into and be used with any shape and/or size of toilet bowl 210, whether it be elongated, round, or even a size not used in the United States. The following descriptions relate to the sample collection device 100 as sized to be used with a standard elongated toilet bowl 210, but it will be understood that one of skill in the art can modify the dimensions and disclosure herein to adapt the sample collection device 100, as disclosed, to be used with any shape and/or size of toilet bowl 210.

Figure 3:
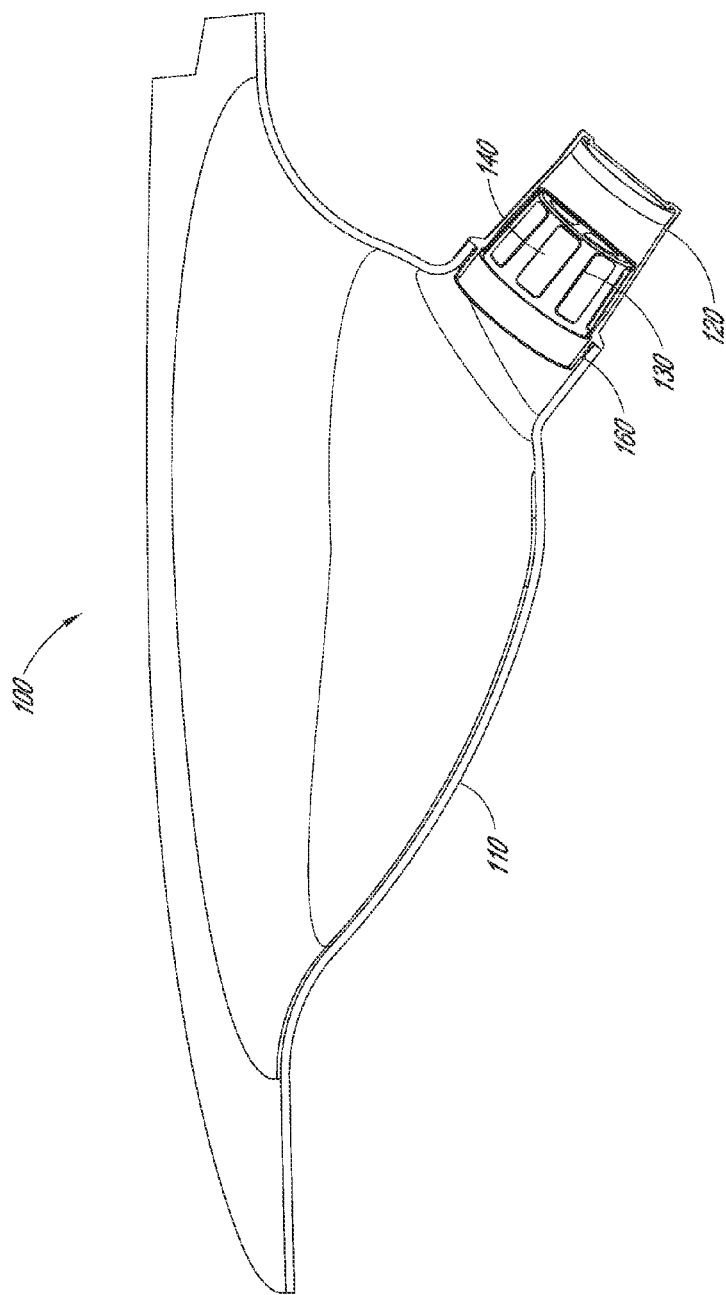
FIG. 3 is a top-biased side cut-away view of one embodiment of a system for collecting samples of human waste products.

FIG. 3 illustrates a cross-sectional view of one embodiment of a sample collection device 100. FIG. 3 shows the sample collection device 100 fully assembled, as described above. In the illustrated embodiment, the screen 140 is inside the collection basket 130 which is placed inside the sample cup 120 to form a sample cup assembly. The sample cup assembly is coupled to the collection bowl 110 at the collector port 150. In the embodiment shown in FIG. 3, the sample cup 120 is coupled to the collector port 150 by a collector port coupler 160. The sample collection device 100 as assembled can be used to collect human waste samples. As discussed above, in one embodiment the collection basket 130 and screen 140 can be excluded from the sample cup assembly.

Figure 4:
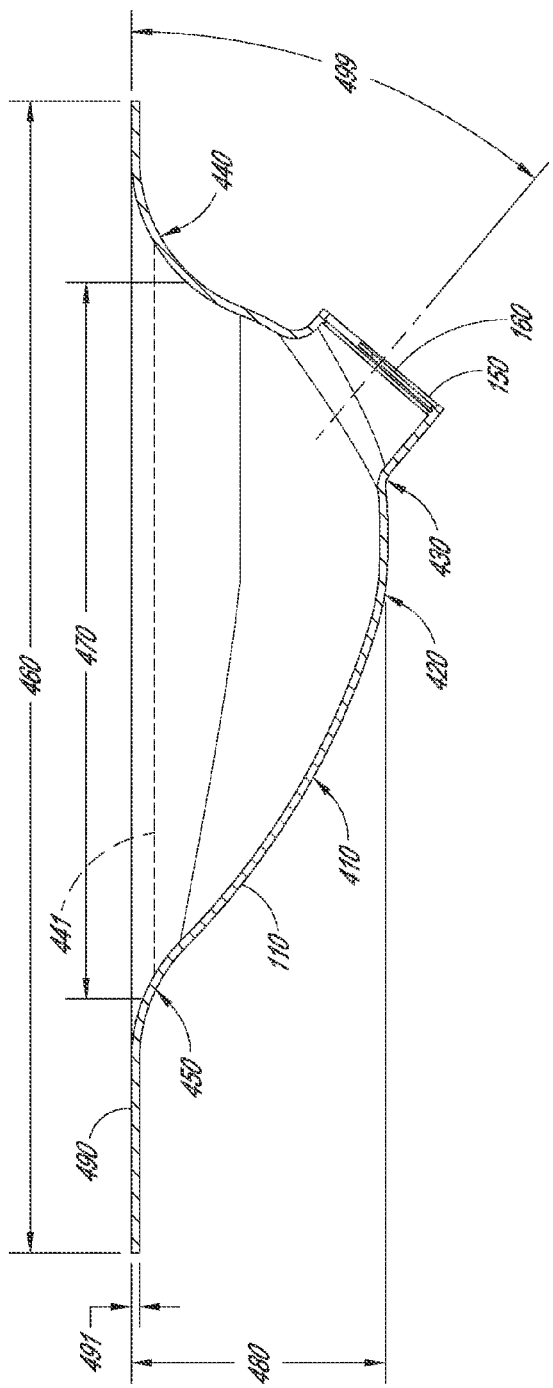
FIG. 4 is a side schematic view of one embodiment of a system for collecting samples of human waste products.

FIG. 4 illustrates a side section view of one embodiment of the sample collection device 100. In particular, FIG. 4 illustrates the shaping and dimensions of one embodiment of the collection bowl 110. The sample collection device 100, can include a collection bowl 110, a collector port 150, a collector port coupler 160, a collection bowl front upper inner radius 410, a collection bowl front lower inner radius 420, a collection bowl front lower outer radius 430, a collection bowl rear outer radius 440, a collection bowl rim 441, a collection bowl front outer radius 450, a sample collection device length 460, a collection bowl length 470, a collection bowl depth 480, a collector seat rim 490, a collector seat rim thickness 491, and a collector port angle 499.

Generally, as illustrated in FIG. 4, the sample collection device 100 can be a U-shaped insert (see FIG. 7A) sized to fit inside a toilet bowl 210 (as shown in FIG. 2). However, in other embodiments, the sample collection device 100 can have other suitable shapes (e.g., round, oval). The sample collection device 100 can have its upper surface defined by a horizontal plane and have a generally bowl shaped depression in its center (a collection bowl 110).

In some embodiments, the sample collection device 100 can be formed monolithically, meaning that it can be formed out of one continuous piece of material. When formed monolithically, the sample collection device 100 can be formed by using such representative, but not limiting, methods as extrusion molding, injection molding, casting, etc. In some embodiments, the sample collection device 100 can be constructed in separate pieces which can then be coupled (e.g., fused) together. For example, the collection bowl 110, the collector seat rim 490, and the collector port 150 can all be made separately then coupled together (e.g., using heat or adhesives, fasteners, etc.).

In some embodiments, the sample collection device 100 has a collector seat rim thickness 491. In some embodiments, the collector seat rim thickness 491 can extend across the entire sample collection device 100 meaning that the entire sample collection device 100 is constructed out of a material having the same thickness. In some embodiments, the collector seat rim thickness 491 can be about 1/16-3/16 inches thick, including about 2/16 inches thick. However, in other embodiments, the collector seat rim thickness 491 can be smaller or greater than the values above. In some embodiments, the collector seat rim thickness 491 can be slightly thicker than the rest of the sample collection device 100 to advantageously provide a stronger rim for the toilet seat ring 215 to hold, thereby holding the entire sample collection device 100 more securely.

In some embodiments, the sample collection device 100 can constructed monolithically out of a plastic, such as but not limited to polyethylene, polypropylene, polystyrene, polyvinyl chloride, polytetrafluoroethylene, and polyamide. In some embodiments, the sample collection device 100 can constructed monolithically out of a metal, such as but not limited to stainless steel or aluminum. In some embodiments, the sample collection device 100 can be constructed out of a composite material, such as by using a fabric or fiber coated with resin. In some embodiments, the sample collection device 100 can be constructed out of any material appropriate for the construction of a waste collection device (e.g., a polymer material, an engineered resin material, a fiberglass material, and a composite material).

In some embodiments, the collection bowl 110 can be defined by a collection bowl front outer radius 450, a collection bowl front upper inner radius 410, a collection bowl front lower inner radius 420, a collection bowl front lower outer radius 430, and a collection bowl rear outer radius 440. In such embodiments, the side profile of the collection bowl 110 can be defined as follows.

The collection bowl 110 surface begins to sink down from the horizontal planar surface of the collector seat rim 490 at a collection bowl front outer radius 450. The collection bowl front outer radius 450 can be in the range of about 1-5 inches, about 1.5-4.5 inches, about 2-4 inches, and about 2.5-3.5 inches, including about 3 inches or any other radius which sizes the sample collection device 100 to fit within a toilet bowl. To properly fit within a toilet bowl, the sample collection device 100 can be of such dimensions that it advantageously does not come in contact with any inner surface of the toilet bowl 210 or the water held in the toilet bowl 210. In some embodiments, it is desirable that such contact not occur to inhibit sample contamination (e.g., minimize the chance of sample contamination). In some embodiments, the only contact between the sample collection device 100 (including the coupled sample cup 120) is the contact between the collector seat rim 490 and the toilet rim 205.

The collection bowl 110 surface then begins to curve towards the horizontal and forms the collection bowl front upper inner radius 410. The collection bowl front upper inner radius 410 can be in the range of about 6-18 inches, about 7-17 inches, about 8-16 inches, about 9-15 inches, about 10-14 inches, and about 11-13 inches, including about 12 inches or any other radius which sizes the sample collection device 100 to fit within a toilet bowl 210 as described above.

At approximately the bottom surface of the collection bowl 110, the collection bowl 110 surface forms a collection bowl front lower inner radius 420 before it begins to curve back upwards to meet the rear side of the sample collection device 100. The collection bowl front lower inner radius 420 can be in the range of about 1.5-5 inches, about 1.7-4.8 inches, about 1.9-4.6 inches, about 2.1-4.4 inches, about 2.3-4.2 inches, about 2.5-4 inches, about 2.7-3.8 inches, about 2.9-3.6 inches, and about 3.1-3.4 inches, including about 3.5 inches or any other radius which sizes the sample collection device 100 to fit within a toilet bowl 210 as described above.

At the bottom of the collection bowl 110, the collection bowl 110 surface bends substantially sharply with a collection bowl front lower outer radius 430 to form the root or base of the collector port 150. The collector port 150 as formed by the substantially sharp bend of the collection bowl front lower outer radius 430 has a luminal axis (e.g., central axis, symmetrical axis) defined by the circumference of the collector port 150. In one embodiment, the collector port 150 can be generally cylindrical. However, in other embodiments, the collector port 150 can have other suitable shapes. The luminal axis of the collector port 150 forms an acute angle collector port angle 499 with the horizontal top surface of the sample collection device 100 and is parallel with the collection bowl 110 surface (or collection bowl 110 wall) after the collection bowl front lower outer radius 430. The collection bowl front lower outer radius 430 can be in the range of about 0.15-0.55 inches, about 0.175-0.525 inches, about 0.2-0.5 inches, about 0.225-0.475 inches, about 0.25-0.45 inches, about 0.275-0.425 inches, about 0.3-0.4 inches, and about 0.325-0.375 inches, including about 0.35 inches or any other radius which sizes the sample collection device 100 to fit within a toilet bowl 210 as described above without touching any of the inner surfaces of the toilet bowl 210 (except, as disclosed above the contact between the collector seat rim 490 and the toilet rim 205).

After the collector port 150, the collection bowl 110 surface curves upward toward the rear of the device with a collection bowl rear outer radius 440. The collection bowl rear outer radius 440 can be in the range of about 1-5 inches, about 1.5-4 inches, and about 2-3 inches, including about 2.5 inches or any other radius which sizes the sample collection device 100 to fit within a toilet bowl 210 as described above.

The collection bowl 110 surface joins with the collector seat rim 490 at the rear of the sample collection device 100 and merges from a curved surface to a surface defined by a horizontal plane which can sit, during operation, on the toilet rim 205.

The collection bowl 110 as defined by the horizontal plane of collector seat rim 490, the collection bowl front outer radius 450, the collection bowl front upper inner radius 410, the collection bowl front lower inner radius 420, the collection bowl front lower outer radius 430, and the collection bowl rear outer radius 440 has a collection bowl depth 480 (the distance from the horizontal plane of the collector seat rim 490 to the bottom of the collection bowl 110). In some embodiments, the collection bowl depth 480 can have a depth of about 2-7 inches, about 2.5-7.25 inches, about 3-6.5 inches, about 3.5-5.75 inches, and about 4-5 inches, including about 4 inches or any other depth which sizes the sample collection device 100 to fit within a toilet bowl 210 as described above.

As disclosed above, the collector port 150 has a luminal axis (e.g., a central axis, or axis of symmetry). In some embodiments, the luminal axis of the collector port 150 of the sample collection device 100 can be critically important to the optimal functioning of the sample collection device 100. As discussed above, some users of the sample collection device 100 can be incontinent, or have bladder control issues. Therefore, in some embodiments, a user may void the entire contents of their bladder into the sample collection device 100 (and as will be apparent, the entire contents of a human bladder can be of a significantly larger volume than the volume of the sample cup 120). In these embodiments, it can be useful for the device to allow the user to easily, cleanly and quickly automatically level the volume in the sample cup 120 to an appropriate, hygienic level. In some embodiments, after the user has voided into the sample collection device 100 a volume greater than the volume of the sample cup 120, the user can level the urine volume contained by the sample cup 120 using the following steps.

The user can void any physiological volume of urine into the sample collection device 100, even overfilling the sample cup 120 (e.g., such that at least some of the urine rests in the volume of the collection bowl 110). After potentially overfilling the sample cup 120 with a sample of urine, the user can pick the device up by the front of the device (e.g., lift the front of the device 100 so that it pivots about its distal edge). As will be apparent by observation of FIG. 4, when the device is held generally vertically (e.g., about 70°, about 80°, about 90°), for example so that the plane defined by the rim 290 is parallel to the force of gravity, the luminal axis of the collector port 150 holds the sample cup 120 at a fixed collector port angle 499 causing at least a portion of the volume contained in the sample collection device 100 and the sample cup 120 to flow out the rear of the sample collection device 100. As is apparent to one of ordinary skill in the art, the collector port angle 499 is inversely proportional to the volume which will remain in the sample cup 120 after holding the sample collection device 100 vertically. The greater the collector port angle 499, the lower is the volume which can remain in the sample cup 120 after holding the sample collection device 100 vertically (with a limit at 90° where the entire contents of the sample cup 120 will exit the sample cup 120 upon holding the sample collection device 100 vertically). As an obvious corollary, the smaller the collector port angle 499, the larger is the volume which can remain in the sample cup 120 after holding the sample collection device 100 vertically. The collector port angle 499 can be in the range of about 10-80°, about 15-75°, about 20-70°, about 25-65°, about 30-60°, about 35-55°, and about 40-50°, including about 45° or any other collector port angle 499 which both sizes the sample collection device 100 to fit within a toilet bowl 210 as described above and positions the collector port 150 to hold the sample cup 120 at an angle appropriate to allow only a portion of the sample cup 120 to be filled with a sample after holding the sample collection device 100 generally vertically (e.g., about 70°, about 80°, about 90°).

The sample collection device 100 has a sample collection device length 460 which can be defined as the length of the sample collection device 100 from the front edge of the device to the back edge of the device. In some embodiments, the sample collection device length 460 can be in the range of about 16-20 inches, about 16.5-19.5 inches, about 17-19 inches, and about 17.5-18.5 inches, including about 18 inches or any other sample collection device length 460 which sizes the sample collection device 100 to fit within a toilet bowl 210 as described above.

In some embodiments, the collection bowl front outer radius 450 and collection bowl rear outer radius 440 define the front and back of the collection bowl rim 441. The collection bowl rim 441 can be an approximation of the upper edge of the collection bowl 110 as it is the apex of the curves which drop down from the collector seat rim 490 (including but not limited to the apexes of the collection bowl front outer radius 450 and the collection bowl rear outer radius 440). The collection bowl rim 441 has, or defines, a collection bowl length 470. In some embodiments, the collection bowl length 470 is just smaller than the length from front to back of a toilet rim 205. In some embodiments, the collection bowl length 470 can be about 8-14 inches, about 8.5-13.5 inches, about 9-13 inches, about 9.5-12.5 inches, about 10-12 inches, and 10.5-11.5 inches, including about 11 inches or any other length which sizes the sample collection device 100 to fit within a toilet bowl 210 as described above.

Figure 5:
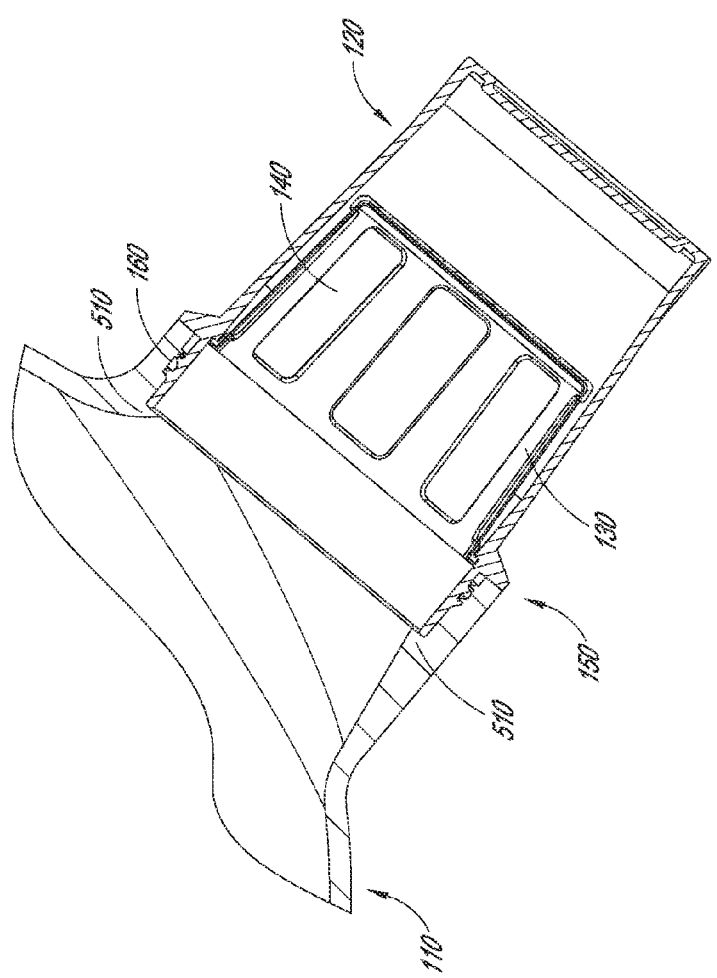
FIG. 5 is an enlarged schematic view of one embodiment of a sample cup coupled to a sample collection bowl.

FIG. 5 illustrates a cross sectional view of a lower portion of one embodiment of the sample collection device 100, specifically the collector port 150. Also shown in FIG. 5 are the screen 140, collection basket 130, and sample cup 120 coupled to the sample collection device 100 via the collector port 150. The lower portion of the sample collection device 100 includes a collector port 150, a collector port coupler 160, and a collector port flange 510. Also shown in the figure are the sample cup 120, collection basket 130, and screen 140.

In operation, the screen 140 and collection basket 130 can be inserted into the sample cup 120 as desired, then the sample cup 120 can be coupled to the collector port 150 via the collector port coupler 160 to effectively seal the sample cup 120 to the sample collection device 100 to collect the sample of interest.

In some embodiments, the collector port coupler 160 of the collector port 150 can be threads that mate with threads on the sample cup 120 (shown in FIG. 5). In other embodiments, the collector port coupler 160 of the collector port 150 can be a pill bottle-style tab and groove structure. In yet other embodiments, the collector port coupler 160 of the collector port 150 can be any other mechanism suitable for releasably coupling the sample cup 120 to the collector port 150 of the collection bowl 110.

In some embodiments, the collector port flange 510 of the collector port 150 can be a stepped flange as illustrated in FIG. 5. The stepped collector port flange 510 of FIG. 5 can serve to act as a stop for the insertion of the sample cup 120 into the collector port 150. When the sample cup 120 is fully inserted into the collector port 150, the upper rim of the sample cup 120 can abut the collector port flange 510 sufficiently tightly such that the collector port flange 510 form a substantially fluid-tight seal with the upper rim of the sample cup 120. The substantially fluid-tight seal created between the collector port flange 510 and the sample cup 120 can advantageously prevent unsanitary sample leakage from the device during use (e.g., leakage between the threads of the collector port 150 and sample cup 120). In some embodiments, the collector port flange 510 is an "L" shaped flange that extends over the lip of the sample cup 120 about the circumference of the collector port 150 to advantageously provide a flow path that extends over the rim of the sample cup 120 thereby preventing the possibility of leakage from the collector port 150 when the sample collection device 100 is in use. In still other embodiments, the collector port flange 510 is any structure which creates a flow path down the surface of the collection bowl 110 through the collector port 150 and into the sample cup 120 which prevents leakage from the collector port 150 while the sample collection device 100 is in use. In still another embodiment (not shown), the sample cup 120 can include an internal threaded portion that can threadably couple to an external threaded portion of the collector port 150, such that the collector port 150 guides a sample into the sample cup 120 during use while inhibiting leakage of sample between the collector port 150 and sample cup 120.

Figure 6:
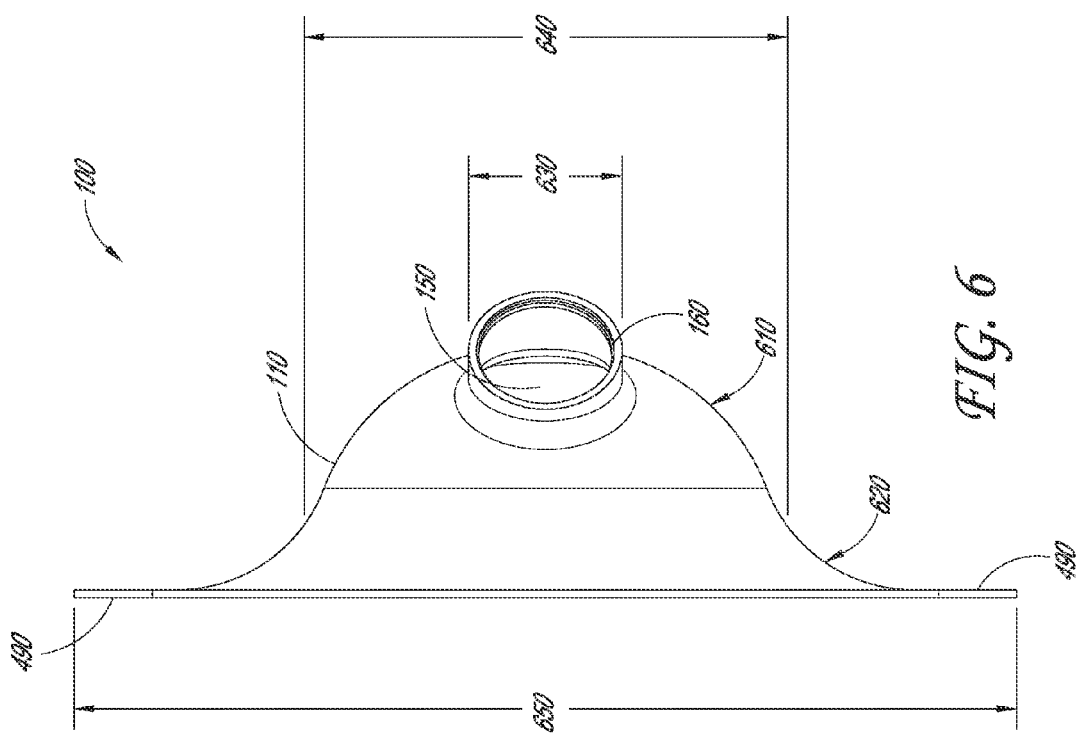
FIG. 6 is a rear schematic view of one embodiment of a system for collecting samples of human waste products.

FIG. 6 illustrates a rear view of one embodiment of the sample collection device 100. In particular, FIG. 6 illustrates the shaping and dimensions of one embodiment of the sample collection device 100. The sample collection device 100, can include a collection bowl 110, a collector port 150, a collector port coupler 160, a collection port diameter 630, a collector seat rim 490, a collection bowl side lower inner radius 610, a collection bowl side upper outer radius 620, and a sample collection device width 650.

In some embodiments, the collection bowl 110 can be defined by a collection bowl side upper outer radius 620 on each side of the collection bowl 110, and a collection bowl side lower inner radius 610 on each side of the collection bowl 110. In some embodiments, the rear profile of the sample collection device 100 can be defined as follows.

The collector seat rim 490, as has been disclosed previously, forms a horizontal planar surface from which the collection bowl 110 extends downward. The collection bowl 110 extends downward from one side at a collection bowl side upper outer radius 620. The collection bowl side upper outer radius 620 can be in the range of about 1.5-4.25 inches, about 1.75-3.75 inches, about 2-3.25 inches, about 2.25-2.75 inches, including about 2.5 inches or any other radius which sizes the sample collection device 100 to fit within a toilet bowl 210. In some embodiments, to properly fit within a toilet bowl, the sample collection device 100 can be of such dimensions that it advantageously does not come in contact with any inner surface of the toilet bowl 210 or the water held in the toilet bowl 210. In some embodiments, it is desirable that such contact not occur to inhibit sample contamination (e.g., minimize the chance of sample contamination). In some embodiments, the only contact between the sample collection device 100 (including the coupled sample cup 120) is the contact between the collector seat rim 490 and the toilet rim 205. Therefore, in the some of the above mentioned embodiments, the collection bowl 110 can extend downward from the collector seat rim 490 just inside the toilet bowl 210 such that the space between the inner wall of the toilet bowl 210 and the outer wall of the collection bowl 110 is minimized.

The collection bowl 110 then curves inward at a collection bowl side lower inner radius 610 to form the bottom of the collection bowl 110. The collection bowl side lower inner radius 610 can be in the range of about 2.5-5.25 inches, about 2.75-4.75 inches, about 3-4.25 inches, about 3.25-3.75 inches, including about 3.5 inches or any other radius which sizes the sample collection device 100 to fit with a toilet bowl 210.

The collection bowl 110 can be symmetric about a front-to-back vertical plane bisecting the center of the collector port 150. Therefore, in some embodiments, the rear profile of the collection bowl 110 is formed by one collection bowl side upper outer radius 620 and one collection bowl side lower inner radius 610 on each side of the sample collection device 100.

As disclosed above, the collection bowl rim 441 can be defined by the curves which drop from the collector seat rim 490. Therefore, in the sample collection device 100 of FIG. 6, the collection bowl rim 441 is defined by the two collection bowl side upper outer radii 620. In some embodiments, the collection bowl side-to-side width 640 is just smaller than the width from side to side of a toilet rim 205. In some of these embodiments, the collection bowl side-to-side width 640 can be in the range of about 5.5-9.5 inches, about 5.75-9.25 inches, about 6-9 inches, about 6.25-8.75 inches, about 6.5-8.5 inches, about 6.75-8.25 inches, about 7-8 inches, and about 7.25-7.75 inches, including about 7.5 inches or any other length which sizes the sample collection device 100 to fit within a toilet bowl 210 as described above.

The sample collection device 100 has a sample collection device width 650 which can be defined as the width of the sample collection device 100 from the left side of the device to the right side of the device (or vise versa). In some embodiments, the sample collection device width 650 can be in the range of about 12-18 inches, about 12.5-17-5 inches, about 13-17 inches, about 13.5-16.5 inches, about 14-16 inches, and about 14.5-15.5 inches, including about 15 inches or any other sample collection device width 650 which sizes the sample collection device 100 to fit within a toilet bowl 210 as described above.

The collector port 150 has a collection port diameter 630 which, because the collector port 150 is circular, can be defined as the distance from one side of the collector port 150 to the other side of the collector port 150. In some embodiments, the collection port diameter 630 can be in the range of about 2-3 inches, and about 2.25-2.75 inches, including about 2.5 inches or any other appropriate collection port diameter 630 to allow the releasable coupling of a sample cup 120 to the collector port 150 using the collector port coupler 160. Urine collection cups in the United States have standardized dimensions. Therefore, such that the sample collection device 100 can be used with such standardized urine collection cups, the collection port diameter 630 can advantageously be sized mate with the threads of a standardized urine collection cup. That is, in some embodiments, the collection port diameter 630 can be about 2.45 inches.

Figure 7A:
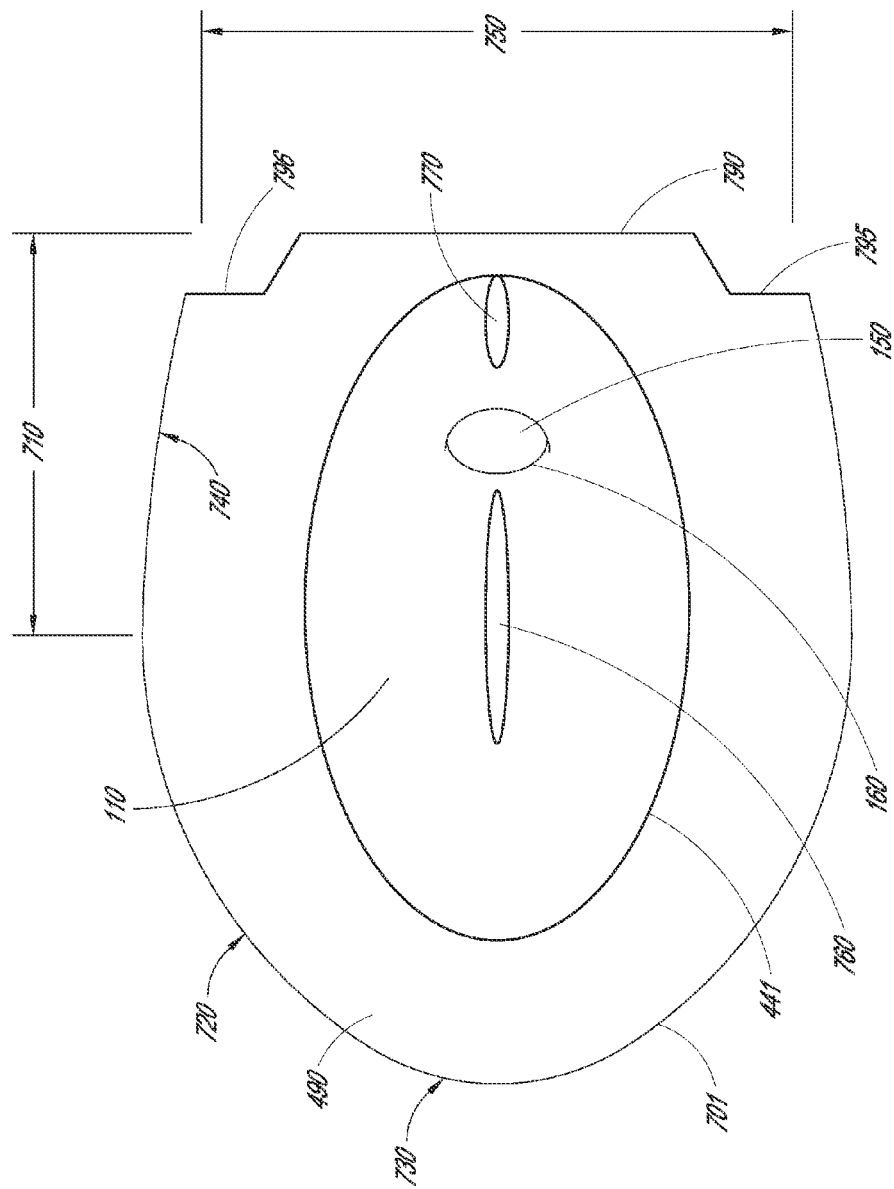
FIG. 7A is a top schematic view of one embodiment of a system for collecting samples of human waste products.

FIG. 7A illustrates a top view of one embodiment of the sample collection device 100. The sample collection device sample collection device 100 can include collector seat rim 490 which, at a collection bowl rim 441, dips down into a collection bowl 110, a U-shaped rim 701, a sample collection device rear-to-side apex length 710, a U-shaped rim front three-quarters radius 720, a U-shaped rim front radius 730, a U-shaped rim rear three-quarters radius 740, a sample collection device rear width 750, an anterior drainage trough 760, a posterior drainage trough 770, a collector back 790, a right rear notch 795, and a left rear notch 796. As discussed above, in other embodiments, the sample collection device 100 can have other suitable shapes (e.g., oval, round), and is not limited to being U-shaped.

As is illustrated by FIG. 7A, the U-shaped rim 701 defines the shape of the collector seat rim 490. The collector seat rim 490 dips down into the collection bowl 110 approximately at the collection bowl rim 441. The collector port 150 exits the collection bowl 110 at the base of the sample collection device 100 and includes a collector port coupler 160 (as discussed previously). The upper perimeter of the U-shaped rim 701 (in the aforementioned horizontal planar surface) and therefore the collector seat rim 490, are defined by the following.

The back of the sample collection device 100 is a substantially flat line with two notches, right rear notch 795 and left rear notch 796. The rear of the sample collection device 100 has a sample collection device rear width 750 which can be in the range of about 10.5-14.5 inches, about 10.75-14.25 inches, about 11-14 inches, about 11.25-13.75 inches, about 11.5-13.5 inches, about 11.75-13.25 inches, about 12-13 inches, and about 12.25-12.75 inches, including about 12.5 inches or any other sample collection device rear width 750 which sizes the sample collection device 100 to fit on a toilet rim 205.

The right rear notch 795 and left rear notch 796 are symmetrical across a left to right plane. In operation, the right rear notch 795 and left rear notch 796 provide a bracing point for the base of sample collection device 100 during the generally vertical (e.g., about 70°, about 80°, about 90°) holding as mentioned previously (e.g., during pivoting of the sample collection device 100 about the rear end to empty the contents of the collection bowl 110 into the toilet). The right rear notch 795 and left rear notch 796 allow a user to simply: finish voiding into the sample collection device 100; lift the toilet seat ring 215; slide the entire sample collection device 100 forward (i.e., toward the user and away from the rear end of the toilet) until the back portion slips into the toilet bowl 210 so that the right rear notch 795 and left rear notch 796 fit over the corners formed by the toilet rim 205; pivot the entire sample collection device 100 on the right rear notch 795 and left rear notch 796 until the sample collection device 100 is oriented generally vertically (e.g., about 70°, about 80°, about 90°) on the right rear notch 795 and left rear notch 796; allow the excess urine to flow out the back of the device; and remove and cap the sample cup 120 from the collector port 150 and collector port coupler 160. The right rear notch 795 and left rear notch 796 allow the process to be dramatically simplified in that the user need not actually pick up the device to use it fully, and therefore it is particularly well suited for individuals with motor disabilities or weakness who would be unable to carefully lift the sample collection device 100. FIGS. 28-35 illustrate an embodiment of the sample collection device 100 (not showing the sample cup 120, collection basket 130, or screen 140) which has both a right rear notch 795 and left rear notch 796. FIGS. 28, 29, 30, and 31 illustrate the right rear notch 795 and left rear notch 796 particularly well.

As mentioned previously, the sample collection device 100 can be bilaterally symmetrical from left to right; therefore only one side of the sample collection device 100 will be discussed. It will be recognized that any statement made about one side of the sample collection device 100 can be applied equally to the other side of the sample collection device 100. The sides of the U-shaped rim 701 extend forward from the rear of the sample collection device 100 (or from the right rear notch 795 or left rear notch 796). The side of the U-shaped rim 701 curves out gently at a U-shaped rim rear three-quarters radius 740 until the sample collection device side apex. The U-shaped rim rear three-quarters radius 740 can be in the range of about 25-39 inches, about 26-38 inches, about 27-37 inches, about 28-36 inches, about 29-35 inches, about 30-34 inches, about 31-33 inches, and about 31.5-32.5 inches, including about 32.93 inches or any other radius which sizes the sample collection device 100 to fit on a toilet rim 205.

As mentioned previously, the point at which the U-shaped rim rear three-quarters radius 740 stops curving out gently is the sample collection device rear-to-side apex. The sample collection device rear-to-side apex length 710 (i.e., the length from the rear of the sample collection device 100 to the rear-to-side apex) can be in the range of about 6.5-10.5 inches, about 6.75-10.25 inches, about 7-10 inches, about 7.25-9.75 inches, about 7.5-9.5 inches, about 7.75-9.25 inches, about 8-9 inches, and about 8.25-8.75 inches, including about 8.5 inches or any other length with sizes the sample collection device 100 to fit on a toilet rim 205.

The U-shaped rim 701 then curves from the sample collection device rear-to-side apex to the front of the sample collection device 100 at a U-shaped rim front three-quarters radius 720. The U-shaped rim front three-quarters radius 720 can be in the range of about 7-13 inches, about 7.5-12.5 inches, about 8-12 inches, about 8.5-11.5 inches, about 9-11 inches, and about 9.5-10.5 inches, including about 10.33 inches or any other radius which sizes the sample collection device 100 to fit on a toilet rim 205.

The U-shaped rim 701 then curves around the front of the sample collection device 100 at a U-shaped rim front radius 730 on its symmetric path back to the rear of the device. The U-shaped rim front radius 730 can be in the range of about 3-7 inches, about 3.25-6.75 inches, about 3.5-6.5 inches, about 3.75-6.25 inches, about 4-6 inches, about 4.25-5.75 inches, about 4.5-5.5 inches, and about 4.75-5.25 inches, including about 5.03 inches or any other radius which sizes the sample collection device 100 to fit on a toilet rim 205.

The sample collection device 100 can include one or more fluid guiding channels, including an anterior drainage trough 760 and/or a posterior drainage trough 770. The anterior drainage trough 760 can be a slightly inset trough that can travel along the plane of bilateral symmetry from just before the collector port 150 (i.e., toward the anterior side of the collector port 150) toward the front of the sample collection device 100. The posterior drainage trough 770 can be a slightly inset trough that can travel along the plane of bilateral symmetry from just after the collector port 150 (i.e., toward the posterior side of the collector port 150) toward the rear of the sample collection device 100. The anterior drainage trough 760 and posterior drainage trough 770 can allow guidance of fluids into and out of the sample cup 120 to make the process even more hygienic and simple. The length of the anterior drainage trough 760 can be in the range of about 1-12 inches, about 2-10 inches, about 3-8 inches, and about 4-6 inches, including about 5 inches. The width of the anterior drainage trough 760 can be in the range of about 0.25-2 inches, about 0.5-1.5 inches, and about 0.75-1 inches. The depth of the anterior drainage trough 760 can be in the range of about 0.125-0.5 inches, and about 0.25-0.375 inches. The length of the posterior drainage trough 770 can be in the range of about 1-6 inches, about 1.5-5 inches, about 2-4 inches, and about 2.5-3 inches. The width of the posterior drainage trough 770 can be in the range of about 0.25-2 inches, about 0.5-1.5 inches, and about 0.75-1 inches. The depth of the posterior drainage trough 770 can be in the range of about 0.125-0.5 inches, and about 0.25-0.375 inches. In some embodiments, neither the anterior drainage trough 760 nor the posterior drainage trough 770 are included in the collection bowl 110 of the sample collection device 100—rather, in these embodiments, the inner surface of the collection bowl 110 is smooth and uniformly curved as described above. FIGS. 28-35 illustrate an embodiment of the sample collection device 100 (without the sample cup 120, collection basket 130, or screen 140) which has a posterior drainage trough 770. FIGS. 28-32 illustrate the posterior drainage trough 770 particularly well.

Figure 7C:
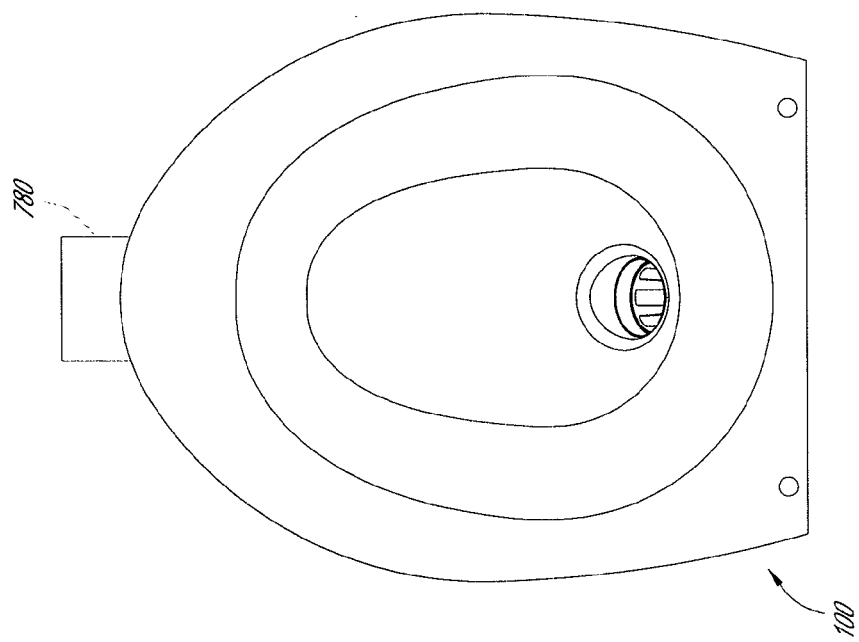
FIG. 7B-7K are schematic views of various embodiments of handles on a system for collecting samples of human waste products.

FIG. 7C illustrates a sample collection device 100 with a first embodiment of a handle 780. The handle 780 on the sample collection device 100 of FIG. 7C can be a substantially rectangular tab extending from the front of the sample collection device 100.

In some embodiments, the handle 780 is substantially a square. In some embodiments, the handle 780 has approximately squared corners. In some embodiments, the handle 780 has rounded corners (as shown in FIG. 7C).

In some embodiments, the handle 780 is constructed monolithically with the sample collection device 100 (i.e., the handle 780 and sample collection device 100 can be formed out of one continuous piece of material). In some embodiments, the handle 780 can be constructed separately from the sample collection device 100 then attached (e.g., fused) to the sample collection device 100. For example, the handle 780 can be made separately from the sample collection device 100, then the handle 780 can be coupled to the sample collection device 100 (e.g., using heat, adhesives, fasteners, etc.).

Just as discussed with regards to the sample collection device 100, in some embodiments, the handle 780 can constructed monolithically out of a plastic, such as but not limited to polyethylene, polypropylene, polystyrene, polyvinyl chloride, polytetrafluoroethylene, and polyamide. In some embodiments, the handle 780 can constructed monolithically out of a metal, such as but not limited to stainless steel or aluminum. In some embodiments, the handle 780 can be constructed out of a composite material, such as by using a fabric or fiber coated with resin. In some embodiments, the handle 780 can be constructed out of any material appropriate for the construction of a waste collection device (e.g., a polymer material, an engineered resin material, a fiberglass material, and a composite material).

Figure 7B:
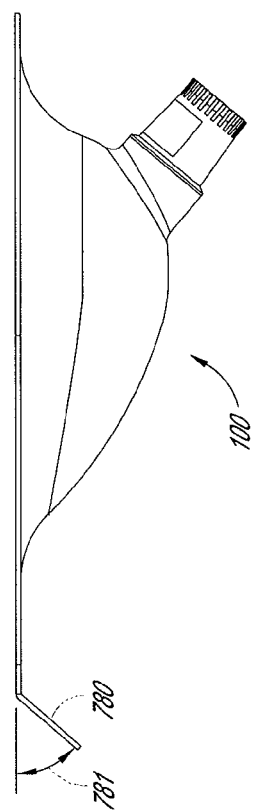

FIG. 7B illustrates a side view of the sample collection device 100 with a first embodiment of a handle 780 shown in FIG. 7C. In some embodiments, the handle 780 extends downward from the horizontal plane defining the top surface of the sample collection device 100. The extension downward is defined by the handle angle 781 (relative to a plane that defines the rim 490 of the sample collection device 100), which can be in the range of about less than 50°, about less than 45°, about less than 40°, about less than 35°, about less than 30°, about less than 25°, about less than 20°, about less than 15°, about less than 10°, and about less than 5°, or any other handle angle 781 which both positions the handle 780 such that in use it does not touch the toilet 201 and allows a user to pick up the device using the handle 780. The handle 780 illustrated in FIG. 7B has a handle angle 781 of about 45°.

A handle 780 as illustrated in FIG. 7B and FIG. 7C can allow a person (e.g., a user) to pick up the device easily without touching the toilet 201 or any portion of the sample collection device 100 which has come in contact with the toilet 201.

Figure 7E:
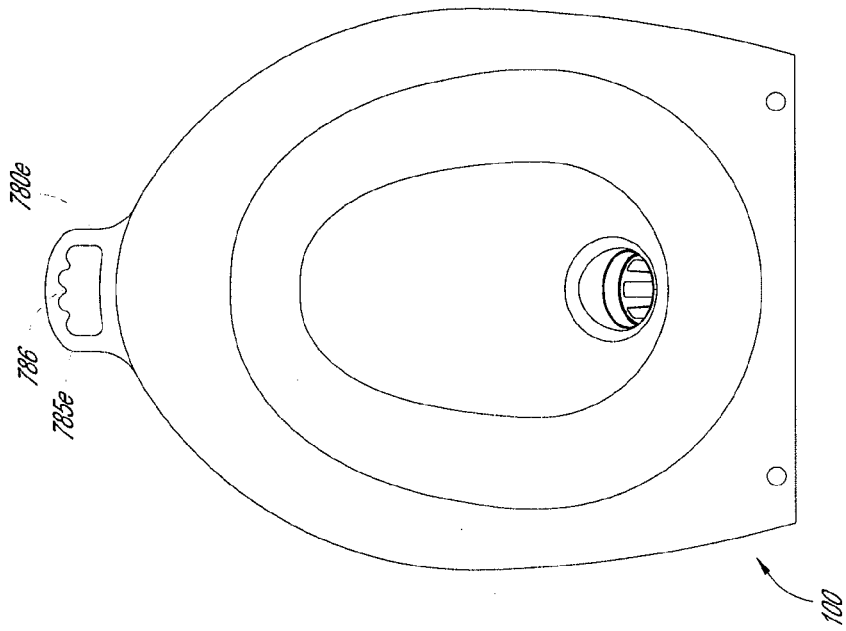

FIG. 7E illustrates a sample collection device 100 with a second embodiment of a handle 780e. The handle 780e on the sample collection device 100 of FIG. 7E can include a curved portion extending from the front of the sample collection device 100 including a handle opening 785e and at least one handle finger inserts 786.

In some embodiments, the handle 780e includes 3 ridges in the handle finger inserts 786. In some embodiments, the handle 780e includes 4 ridges in the handle finger inserts 786. In some embodiments, the handle 780e includes 5 ridges in the handle finger inserts 786.

Figure 7D:
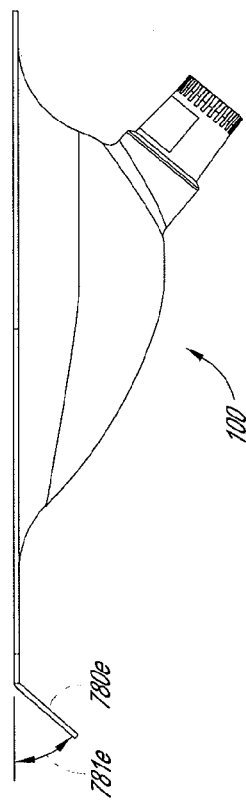

FIG. 7D illustrates a side view of the sample collection device 100 with a second embodiment of a handle 780e shown in FIG. 7E. In some embodiments, the handle 780e can extend downward from the horizontal plane defining the top surface of the sample collection device 100. The extension downward is defined by the handle angle 781e (relative to a plane that defines the rim 490 of the sample collection device 100), which can be in the range of about less than 50°, about less than 45°, about less than 40°, about less than 35°, about less than 30°, about less than 25°, about less than 20°, about less than 15°, about less than 10°, and about less than 5°, or any other handle angle 781e which both positions the handle 780e such that in use it does not touch the toilet 201 and allows a user to pick up the device using the handle 780e. The handle 780 illustrated in FIG. 7D (i.e., handle 780e) has a handle angle 781e of about 20°.

A handle 780 as illustrated in FIG. 7D and FIG. 7E can allow a person (e.g., a user) to pick up the device easily without touching the toilet 201 or any portion of the sample collection device 100 which has come in contact with the toilet 201.

Figure 7G:
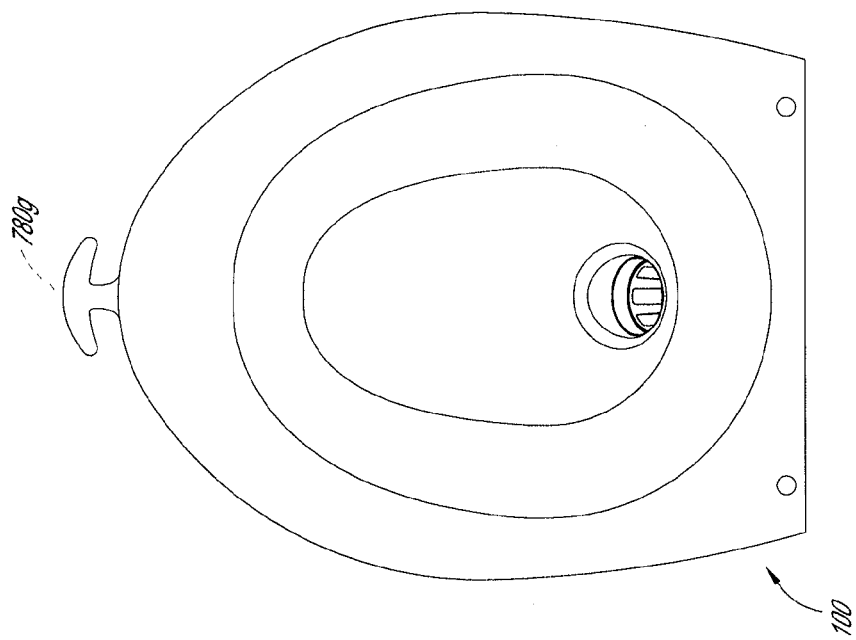

FIG. 7G illustrates a sample collection device 100 with a third embodiment of a handle 780g. The handle 780g on the sample collection device 100 of FIG. 7G can include a post extending from the front of the sample collection device 100 and a curved portion at the end of the post. As shown in FIG. 7G, the handle 780g can resemble a capital "T" with a curved top.

Figure 7F:
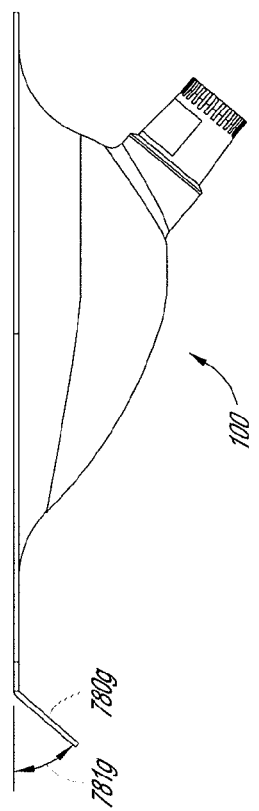

FIG. 7F illustrates a side view of the sample collection device 100 with a third embodiment of a handle 780g shown in FIG. 7G. In some embodiments, the handle 780g can extend downward from the horizontal plane defining the top surface of the sample collection device 100. The extension downward is defined by the handle angle 781g (relative to a plane that defines the rim 490 of the sample collection device 100), which can be in the range of about less than 50°, about less than 45°, about less than 40°, about less than 35°, about less than 30°, about less than 25°, about less than 20°, about less than 15°, about less than 10°, and about less than 5°, or any other handle angle 781g which both positions the handle 780g such that in use it does not touch the toilet 201 and allows a user to pick up the device using the handle 780g. The handle 780 illustrated in FIG. 7F (i.e., handle 780g) has a handle angle 781g of about 25°.

A handle 780 as illustrated in FIG. 7F and FIG. 7G can allow a person (e.g., a user) to pick up the device easily without touching the toilet 201 or any portion of the sample collection device 100 which has come in contact with the toilet 201.

Figure 7I:
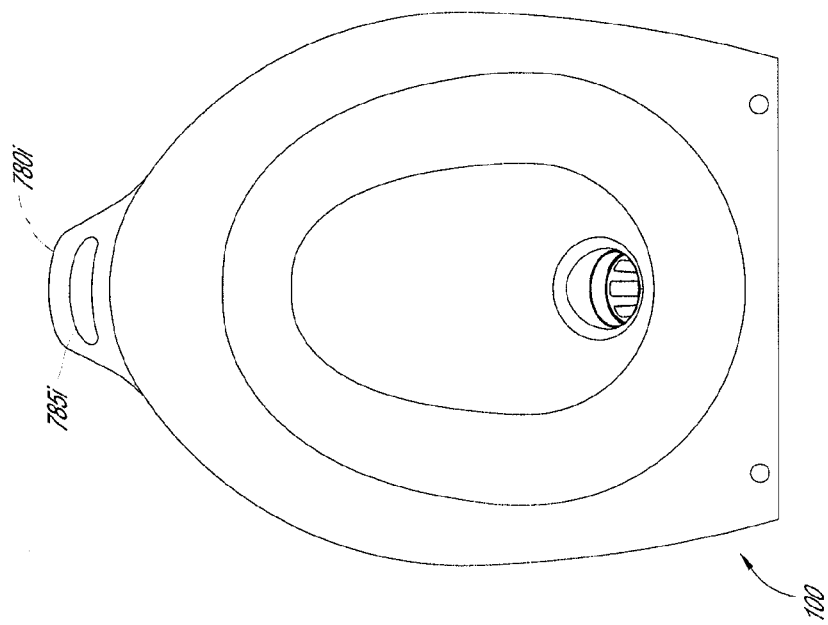

FIG. 7I illustrates a sample collection device 100 with a fourth embodiment of a handle 780i. The handle 780i on the sample collection device 100 of FIG. 7I can include a curved portion extending from the front of the sample collection device 100 including a handle opening 785i.

Figure 7H:
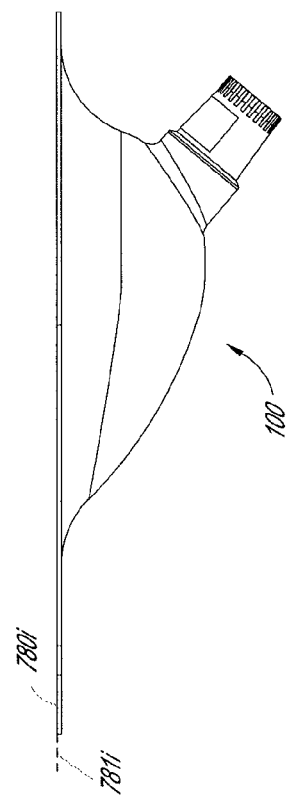

FIG. 7H illustrates a side view of the sample collection device 100 with a fourth embodiment of a handle 780i shown in FIG. 7I. In some embodiments, the handle 780*i* can extend downward from the horizontal plane defining the top surface of the sample collection device 100. The extension downward is defined by the handle angle 781*i* (relative to a plane that defines the rim 490 of the sample collection device 100), which can be in the range of about less than 50°, about less than 45°, about less than 40°, about less than 35°, about less than 30°, about less than 25°, about less than 20°, about less than 15°, about less than 10°, and about less than 5°, or any other handle angle 781*i* which both positions the handle 780*i* such that in use it does not touch the toilet 201 and allows a user to pick up the device using the handle 780*i*. The handle 780 illustrated in FIG. 7H (i.e., handle 780*i*) has a handle angle 781*i* of about 0°.

A handle 780 as illustrated in FIG. 7H and FIG. 7I can allow a person (e.g., a user) to pick up the device easily without touching the toilet 201 or any portion of the sample collection device 100 which has come in contact with the toilet 201.

Figure 7K:
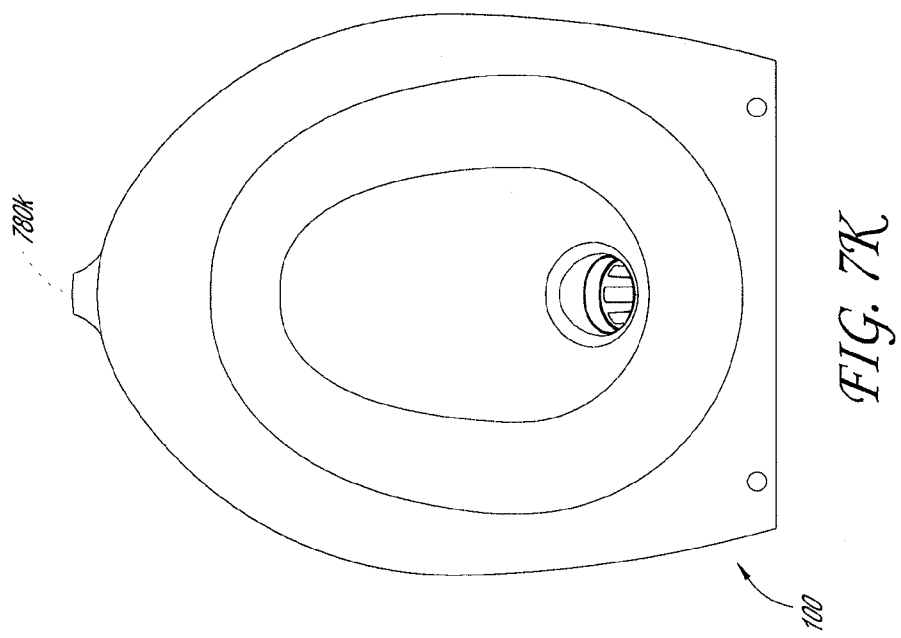

FIG. 7K illustrates a sample collection device 100 with a fifth embodiment of a handle 780*k*. The handle 780*k* on the sample collection device 100 of FIG. 7K can include a curved tab portion extending from the front of the sample collection device 100. In some embodiments, the handle 780*k* can have a side-to-side width of about 1-3 inches, and about 1.5-2.5 inches, including about 2 inches. In some embodiments, the handle 780*k* can have a front to back depth of about 0.5-1 inches, including about 0.75 inches. In other embodiments, the handle 780*k* can have other suitable dimensions, including a width and/or depth that is smaller or greater than these values.

Figure 7J:
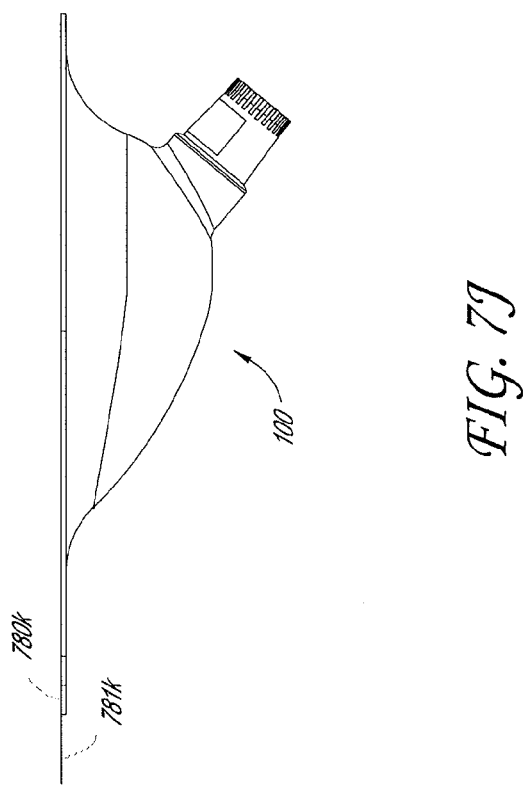

FIG. 7J illustrates a side view of the sample collection device 100 with a fifth embodiment of a handle 780*k* shown in FIG. 7K. In some embodiments, the handle 780*k* can extend downward from the horizontal plane defining the top surface of the sample collection device 100. The extension downward is defined by the handle angle 781*k* (relative to a plane that defines the rim 490 of the sample collection device 100), which can be in the range of about less than 50°, about less than 45°, about less than 40°, about less than 35°, about less than 30°, about less than 25°, about less than 20°, about less than 15°, about less than 10°, and about less than 5°, or any other handle angle 781*k* which both positions the handle 780*k* such that in use it does not touch the toilet 201 and allows a user to pick up the device using the handle 780*k*. The handle 780 illustrated in FIG. 7J (i.e., handle 780*k*) has a handle angle 781*k* of about 0°.

A handle 780 as illustrated in FIG. 7J and FIG. 7K can allow a person (e.g., a user) to pick up the device easily without touching the toilet 201 or any portion of the sample collection device 100 which has come in contact with the toilet 201.

Figure 8A:
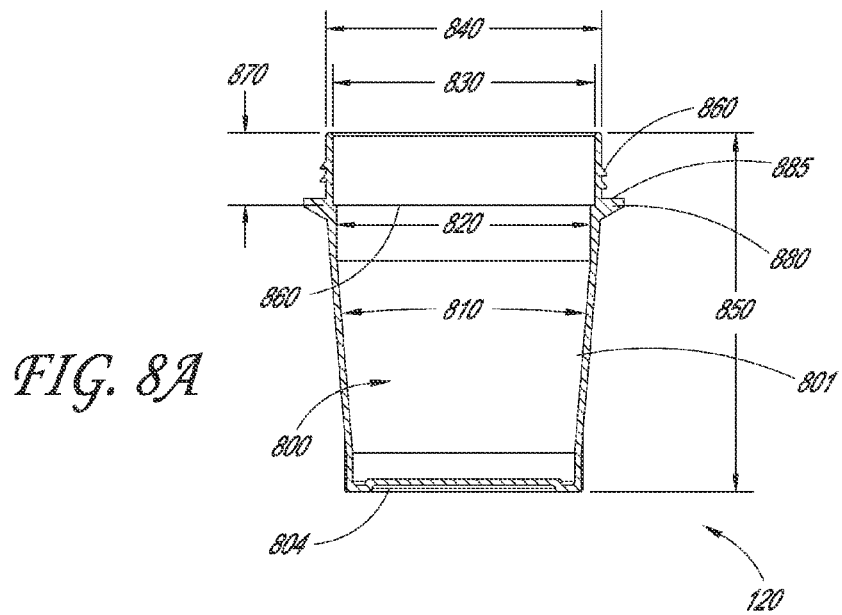
FIGS. 8A, 8B, and 8C are schematic views of one embodiment of a sample cup.
Figure 8B:
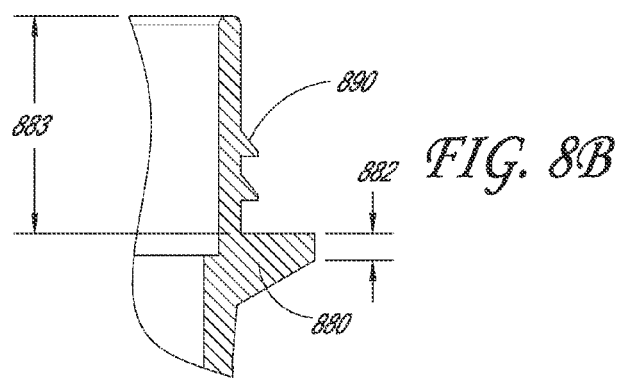
Figure 8C:
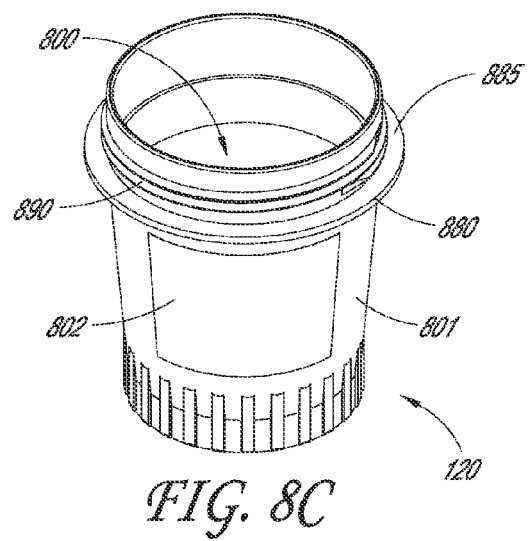

FIGS. 8A, 8B and 8C illustrate varying views of one embodiment of a sample cup 120. The sample cup 120 as illustrated in FIGS. 8A-8C can include a collection volume 800, a cup wall 801, a cup label 802, a sample cup mouth 803, a sample cup base 804, a cup wall angle 810, a cup upper diameter 820, a cup rim inner diameter 830, a cup rim outer diameter 840, a cup height 850, a basket holding rim 860, a basket holding rim inset depth 870, a sample cup flange 880, a sample cup flange depth 882, a sample cup rim inset depth 883, a sample cup flange seat 885, and sample cup threads 890. The sample cup 120, simply, is a cup with a cup wall 801 rising from a sample cup base 804 and with sample cup threads 890 encircling a sample cup mouth 803.

In operation, the sample cup 120 can be removably coupled to the collection bowl 110 of the sample collection device 100 using the collector port coupler 160 of the collector port 150. A user may then fill the sample cup 120 with a sample as discussed above. In further operation, the sample cup 120 can be de-coupled from the collector port coupler 160 of the collector port 150 and a cap applied to store the sample contained within the sample cup 120.

FIG. 8A illustrates a cross sectional view through the center of one embodiment of the sample cup 120. Shown in FIG. 8A are a collection volume 800, a cup wall 801, a sample cup mouth 803, a sample cup base 804, a cup wall angle 810, a cup upper diameter 820, a cup rim inner diameter 830, a cup rim outer diameter 840, a cup height 850, a basket holding rim 860, a basket holding rim inset depth 870, and a sample cup threads 890.

In some embodiments, the sample cup 120 can constructed monolithically out of a plastic, such as but not limited to polyethylene, polypropylene, polystyrene, polyvinyl chloride, polytetrafluoroethylene, and polyamide. In some embodiments, the sample cup 120 can constructed monolithically out of a metal, such as but not limited to stainless steel or aluminum. In some embodiments, the sample cup 120 can be constructed out of a composite material, such as by using a fabric or fiber coated with resin. In other embodiments, the sample cup 120 can be made of other suitable materials (e.g., a polymer material, an engineered resin material, a fiberglass material, and a composite material).

In the illustrated embodiment, the cup wall 801 rises up from the sample cup base 804 with an increasing diameter (formed by the cup wall angle 810). As shown in FIG. 8A, the sample cup 120 has a cup wall angle 810, a cup upper diameter 820, a cup rim inner diameter 830 and a cup rim outer diameter 840. The cup wall angle 810 can be in the range of about 5-13° off vertical, about 6-12° off vertical, about 7-11° off vertical, and about 8-10° off vertical, including about 9° off vertical. The cup wall angle 810 causes the diameter of the cup to be greater the higher up the cup wall the diameter is measured. The cup upper diameter 820 can be in the range of about 1.5-2.5 inches, about 1.6-2.4 inches, about 1.7-2.3 inches, about 1.8-2.2 inches, and about 1.9-2.1 inches, including about 1.942 inches or any other diameter which permits the sample cup 120 to couple with the collector port coupler 160. By comparison, the cup rim inner diameter 830 (which is measured higher up the cup wall 801) can be in the range of about 1.9-2.2 inches, including about 2.0-2.1 inches or any other diameter which permits the sample cup 120 to couple with the collector port coupler 160.

The cup rim outer diameter 840 of the sample cup 120 can be substantially the same size as the inner diameter of the collector port coupler 160 thereby allowing the sample cup 120 to removably couple with the collector port coupler 160. The cup rim outer diameter 840 can be in the range of about 2-3 inches, and about 2.25-2.75 inches, including about 2.11 inches or any other appropriate cup rim outer diameter 840 to allow the releasable coupling of a sample cup 120 to the collector port 150 using the collector port coupler 160. In another embodiment, as discussed above, the sample cup 120 can couple to the connector port 150 such that the connector port 150 at least partially extends into the sample cup 120 (e.g., the cup rim inner diameter 830 is greater than the collection port diameter 630).

The cup wall 801 rises up from the sample cup base 804 to a cup height 850. The cup height 850 can be in the range of about 1.75-3.75 inches, about 2-3.5 inches, about 2.25-3.25 inches, and about 2.5-3 inches including about 2.75 inches or any other cup height 850 which allows the sample collection device 100 to be sizes to fit within a toilet bowl 210 as described above.

In some embodiments, the sample cup flange 880 can disrupt the outer vertical surface of the sample cup 120 in a horizontal ring-like fashion. In operation in accordance with some embodiments, the sample cup flange 880 abuts the base of the collector port 150 (as shown in FIG. 5) and the upper rim of the sample cup 120 abuts the collector port flange 510 of FIG. 5. Therefore, sample cup rim inset depth 883 is the portion of cup height 850 that can couple with collector port coupler 160. In some embodiments, the sample cup rim inset depth 883 can be in the range of about 0.3-0.7 inches, about 0.4-0.6 inches, and about 0.5 inches, including about 0.55 inches or any other distance which sizes the sample cup 120 to allow the releasable coupling of sample cup 120 to the collector port 150.

In some embodiments, the sample cup 120 can include a basket holding rim 860 disposed a basket holding rim inset depth 870 from the top of the sample cup 120. The basket holding rim 860 can hold a collection basket 130 in place (particularly, as will be discussed later, when the collection basket 130 includes a flange around it outer upper edge). In some embodiments, the basket holding rim inset depth 870 can be in the range of about 0.3-0.7 inches, about 0.4-0.6 inches, and about 0.5 inches, including about 0.55 inches or any other distance which sizes the sample cup 120 to allow the seating of the screen 140 within the interior of the sample cup 120.

FIG. 8B illustrates an enlarged view of the coupling area of one embodiment of the sample cup 120. The coupling area shown includes sample cup threads 890 which can thread into a threaded collector port coupler 160. In some embodiments, the coupling element of the sample cup 120 can be threads that mate with threads on the collector port coupler 160 (shown in FIG. 5). In other embodiments, the coupling element of the sample cup 120 can be a pill bottle-style tab and groove structure. In yet other embodiments, the coupling element of the sample cup 120 can be any other mechanism capable of removably coupling the sample cup 120 to the collector port 150 of the collection bowl 110.

FIG. 8C illustrates a perspective view of one embodiment of the sample cup 120. Shown in FIG. 8C are the cup wall 801 which, in this embodiment, has a cup label 802, a sample cup flange 880 with a sample cup flange seat 885 where the base of the collector port coupler 160 seats, sample cup threads 890 which mate with the threads of the collector port coupler 160 (in a threaded embodiment), and the collection volume 800.

Sample cups used for medical applications, particularly for waste samples, are broadly standardized across the United States (and other locations as well). Therefore, in some embodiments, the sample cup 120 can have at least the same coupling mechanism as a standardized sample cup to advantageously permit interchangeability of the two. In such embodiments, the many parameters could be varied from the standardized cup, including but not limited to cup height 850, collection volume 800, etc. In some embodiments, the sample cup 120 can have the same specifications as the standardized cup.

Figure 9A:
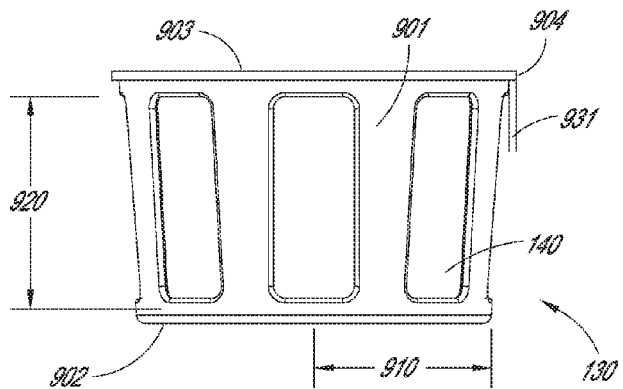
FIGS. 9A, 9B, and 9C are schematic views of one embodiment of a collection basket.
Figure 9B:
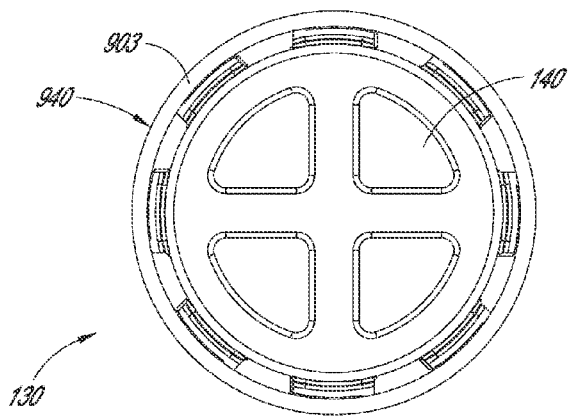
Figure 9C:
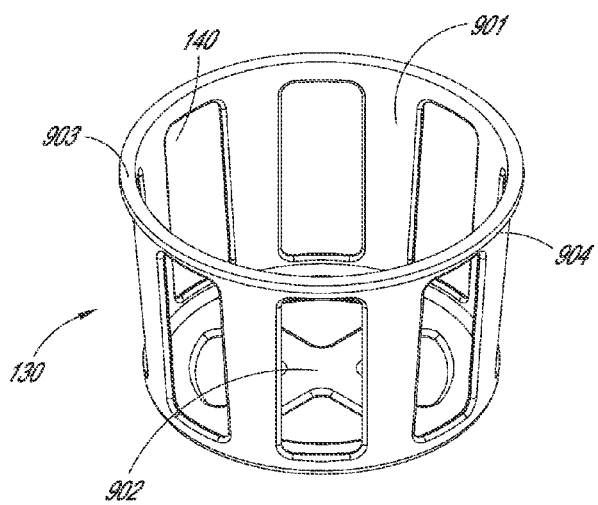

FIGS. 9A, 9B, and 9C illustrate various views of one embodiment of a collection basket 130 with a screen 140. The collection basket 130 and screen 140 as illustrated in FIGS. 9A-9C can include at least one basket slat 901, a basket bottom 902 a basket rim 903, a basket rim flange 904, a basket radius 910, a basket depth 920, a basket rim flange width 931, a basket rim outer radius 940.

In operation, the collection basket 130 and screen 140 can be simply slipped into the sample cup 120 which can, as described above, be removably coupled to the collection bowl 110 of the sample collection device 100 using the collector port coupler 160 of the collector port 150. A user may then fill the sample cup 120 with a sample as discussed above. In further operation, the collection basket 130 and screen 140 serve to filter the sample, thereby keeping large particulate matter out of the sample. In operation, the collection basket 130 and screen 140 can be used to catch kidney stones. In further operation, the sample cup 120 (with the collection basket 130 and screen 140 inside) can be de-coupled from the collector port coupler 160 of the collector port 150 and a cap applied to store the sample contained within the sample cup 120. The collection basket 130 and screen 140 can serve to keep the particulate matter separate from the liquid sample.

FIG. 9A illustrates a side view of one embodiment of a collection basket 130 with screen 140 installed. Shown in FIG. 9A are at least one basket slat 901, a basket bottom 902, a basket rim flange 904, a basket rim flange width 931, a basket rim 903, a side screen port 943, a basket rim depth 930 and a basket depth 920. Simply, the collection basket 130 is formed by at least one basket slat 901 rising from the basket bottom 902 connected at their top by a basket rim 903.

In some embodiments, the collection basket 130 can constructed monolithically out of a plastic, such as but not limited to polyethylene, polypropylene, polystyrene, polyvinyl chloride, polytetrafluoroethylene, and polyamide. In some embodiments, the collection basket 130 can constructed monolithically out of a metal, such as but not limited to stainless steel or aluminum. In some embodiments, the collection basket 130 can be constructed out of a composite material, such as by using a fabric or fiber coated with resin. In other embodiments, the collection basket 130 can be made of other suitable materials (e.g., a polymer material, an engineered resin material, a fiberglass material, and a composite material).

In some embodiments, the screen 140 can be constructed out of wire (e.g., a fine metallic wire screen). In other embodiments, the screen 140 can be constructed out of fabric or a porous spongy material. In yet other embodiments, the screen 140 can be constructed out of natural fibers, such as but not limited to silk. In some embodiments, the material out of which the screen 140 is constructed can have a small pore size to advantageously trap particulate matter. In some embodiments, the pore size of the screen 140 can be in the range of about 5-500 µm, about 15-450 µm, about 25-400 µm, about 35-350 µm, about 45-300 µm, about 55-250 µm, about 65-200 µm, about 75-150 µm, and about 85-100 µm, including any pore size which causes the screen 140 to catch particulate material in the sample.

In some embodiments, the screen 140 can be a solid piece of screen 140 lining the collection basket 130. In other embodiments, the screen 140 can be discrete pieces of screen 140 only covering the holes in the collection basket 130 (attached or fused to the collection basket 130 around the holes in the collection basket 130). In other embodiments, as discussed above the collection basket 130 and screen 140 can be a single piece (e.g., monolithic). In still other embodiments, one or both of the collection basket 130 and screen 140 can be excluded); for example, in some embodiments the collection basket 130 can be excluded and the screen 140 can have a flange that rests on the rim 860 in the sample cup 120.

In some embodiments, the basket bottom 902 can have a radius of about 0.675-1.075 inches, and about 0.775-0.975 inches, including about 0.875 inches or any other radius which sizes the collection basket 130 to fit inside the sample cup 120.

In some embodiments, the collection basket 130 has a basket rim outer radius 940 which can be seated against the basket holding rim 860 of the sample cup 120. In these embodiments the outer diameter of the basket rim 903 (defined by the basket rim outer radius 940) can be substantially equivalent to the inner diameter of the basket holding rim 860 of the sample cup 120. In some embodiments, the basket rim outer radius 940 can be in the range of about 1.5-2.5 inches, and about 1.75-2.25 inches, including about 2 inches or any other radius which allows the collection basket 130 to seat down into the sample cup 120. As illustrated in FIG. 9A, the basket rim flange 904 of the basket rim 903 can seat directly onto the basket holding rim 860 of the sample cup 120 to keep the collection basket 130 in place while in operation within the sample cup 120. The basket rim flange 904 has a basket rim flange width 931 which can be in the range of about 0.02-0.06 inches, and about 0.03-0.05 inches, including about 0.04 inches or any other width with sizes the basket rim flange 904 to seat onto the basket holding rim 860 of the sample cup 120.

It will be understood by one of ordinary skill in the art that there can be any of a number of possible collection basket 130 and screen 140 designs which can work equally well in this particular situation. The operative function is that the basket rim outer radius 940 seats substantially firmly against the inner portion of the cup wall 801 of the sample cup 120 such that substantially the entire sample flows through the screen 140 so as to catch substantially all existing particulate matter. The collection basket 130 as shown is only one possible embodiment of a collection basket 130 and includes several design features that are not crucial to its function, including the number of basket slat 901, the shape of the screen 140 ports, etc. Any collection basket 130 which serves to filter substantially all particulate matter from a liquid sample is anticipated by this disclosure.

Figure 10A:
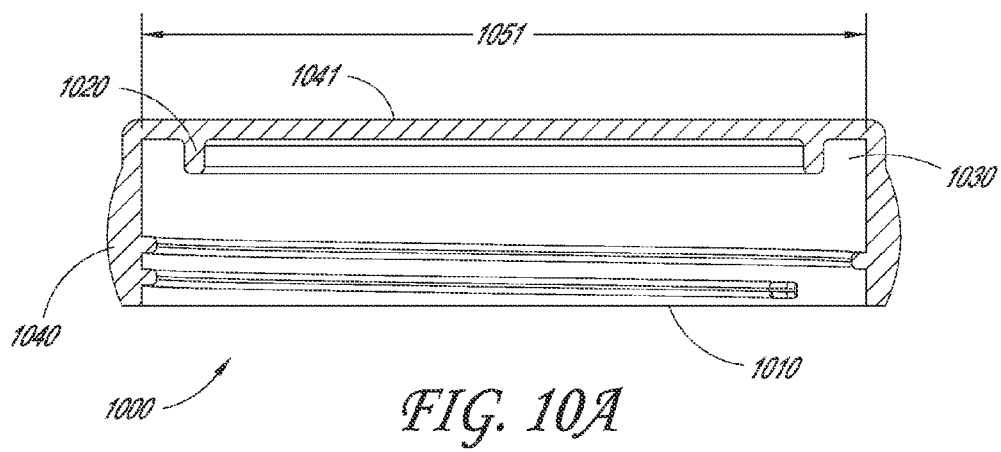
FIGS. 10A, and 10B are schematic views of one embodiment of a collection cup cap.
Figure 10B:
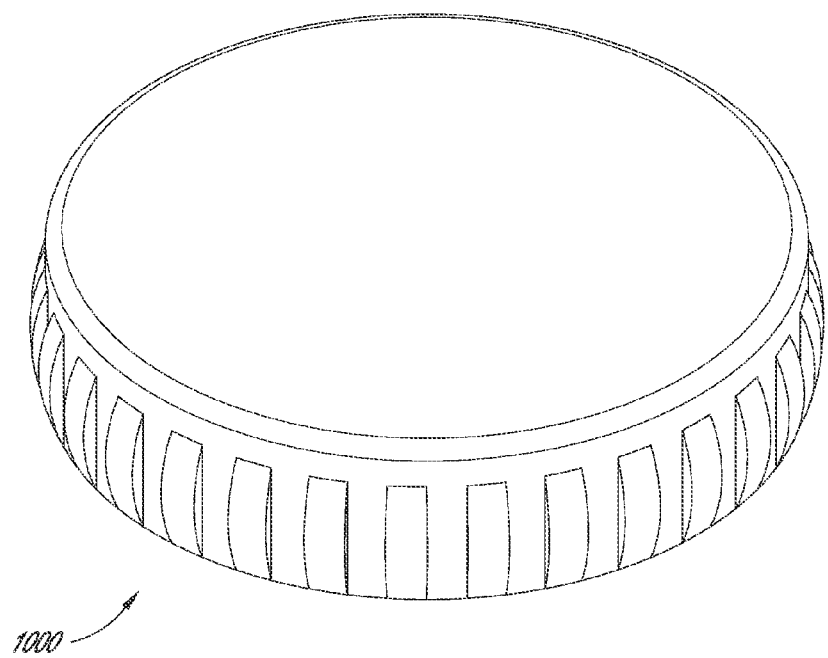

FIGS. 10A and 10B illustrate various views of one embodiment of a collection cup cap 1000. The collection cup cap 1000, as illustrated in FIG. 10A-10B can include a cap wall 1040, a cap top 1041, cap threads 1010, and a cup rim inset 1030 formed by a cap inner flange 1020, and a cap inner diameter 1051.

The collection cup cap 1000 can simply be a cap for the sample cup 120 having cap walls 1040 with a cap top 1041. The inside surface of the cap wall 1040 can have a coupling element to match the coupling element on the sample cup 120 (therefore, it can be the same coupling element as the collector port coupler 160 of the collector port 150). FIG. 10A illustrates a collection cup cap 1000 with cap threads 1010 which can mate with the sample cup threads 890 of the sample cup 120.

In some embodiments, there can be a cap inner flange 1020 running in a ring on the inside of the cap top 1041. The cap inner flange 1020 can create a cup rim inset 1030 which can accept the upper rim of the cup wall 801 of the sample cup 120 to advantageously create a substantially fluid tight seal thereby preventing leakage once the collection cup cap 1000 has been applied to the sample cup 120.

In some embodiments, the collection cup cap 1000 can have a cap inner diameter 1051 that substantially matches the outer diameter of the upper rim of the cup wall 801 of the sample cup 120.

As discussed with respect to the sample cup 120, collection cup caps used for sample cups in medical applications, particularly for waste samples, are broadly standardized across the United States (and other locations as well). Therefore, in some embodiments, collection cup cap 1000 can have a coupling mechanism which can mate with a standardized sample cup. In some embodiments, the collection cup cap 1000 can have the same specifications as a standardized collection cup cap.

Figure 11:
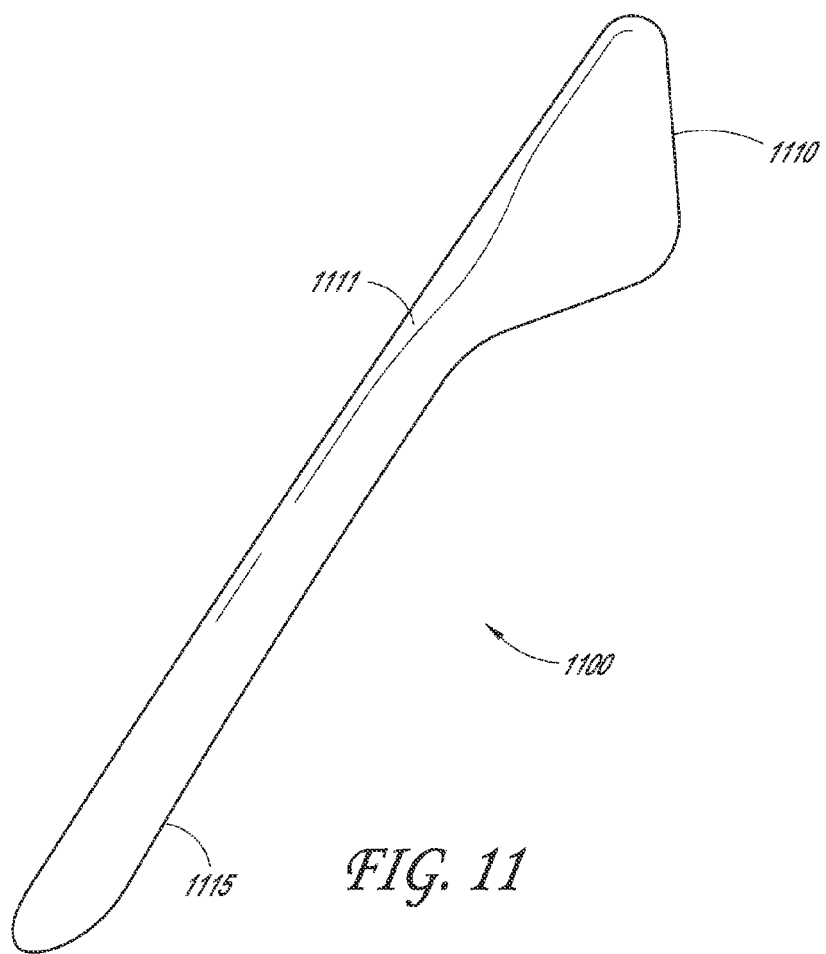
FIG. 11 is a schematic view of one embodiment of a sample spatula.

FIG. 11 illustrates a one embodiment of a sample spatula 1100. The sample spatula 1100, as illustrated in FIG. 11 can include a spatula blade 1110, a spatula spine 1111, and a spatula handle 1115. The wide, flat spatula blade 1110 is disposed on the end of the spatula handle 1115. The sample spatula 1100 can have a spatula spine 1111 to advantageously add additional strength to the sample spatula 1100.

In operation, the sample spatula 1100 can be used primarily for stool specimens. Frequently stools can be relatively hard or sticky. Such stools can be difficult to place within the sample cup 120. Therefore, in operation, the spatula blade 1110 of the sample spatula 1100 can be used to scoop a sample of the stools into the sample cup 120 (e.g., push the stool sample into the sample cup 120 while the sample collection device 100 is sitting on the toilet 201).

In some embodiments, the sample spatula 1100 can be constructed monolithically out of a plastic, such as but not limited to polyethylene, polypropylene, polystyrene, polyvinyl chloride, polytetrafluoroethylene, and polyamide. In some embodiments, the sample collection device 100 can constructed monolithically out of a metal, such as but not limited to stainless steel or aluminum.

In some embodiments, the sample spatula 1100 can include a spatula spine 1111 to advantageously provide additional lateral strength for the user to scoop a sample. In other embodiments, the sample spatula 1100 does not include a spatula spine 1111.

In some embodiments, the spatula blade 1110 can be a flat blade with a flattened edge (as shown in FIG. 11). In other embodiments, the spatula blade 1110 can be a flat blade with a curved edge. In yet other embodiments, the spatula blade 1110 can be a blade of any shape which allows a user to scoop a stool sample and place it within a sample cup 120.

Sample Collection Kit Embodiment

In some embodiments, a sample collection kit can be provided to a user. The sample collection kit can comprise a sample collection device 100, a sample cup 120, a collection basket 130 and screen 140, and a sample spatula 1100 (or any combination thereof). In some embodiments, prior to being provided to the user, the individual pieces of the sample collection kit can be appropriately sterilized. Additionally, in accordance with some embodiments, the appropriately sterilized sample collection kit can be hermetically sealed as a single unit, thereby advantageously maintaining the sterilization of the sample collection kit. The user, depending on his or her needs, can then select which components of the kit should be used to collect his or her sample.

Method of Use for Urine Samples

Figure 12:
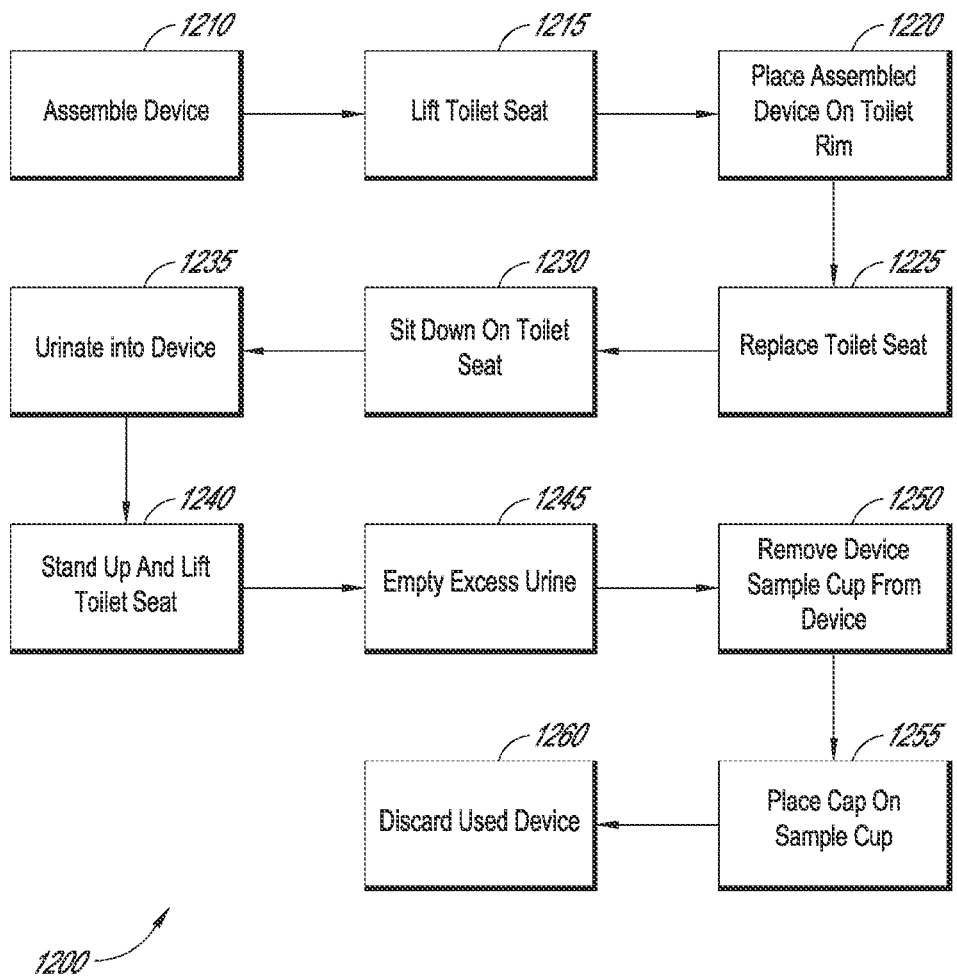
FIG. 12 is a flow chart of one embodiment of a method for collecting a urine sample using a system for collecting samples of human waste products.

FIG. 12 illustrates a method of collecting a urine sample using the sample collection device 100 disclosed herein 1200.

First, at step 1210, a person (e.g., user, medical assistant) assembles the sample collection device 100. Generally, for a urine sample only the sample cup 120 is necessary along with the collection bowl 110. Neither the collection basket 130 and screen 140 nor the sample spatula 1100 are necessary for a simple urine sample collection.

In some embodiments, the collection basket 130 and screen 140 are used in addition to the sample cup 120 and the collection bowl 110. In this manner it can be possible to catch kidney stones or solid particulate matter to keep it separated from the urine sample in the sample cup 120.

Next, at step 1215, a person (e.g., the user) lifts the toilet seat ring 215 of FIG. 2 of the toilet 201 of FIG. 2. Both the lid and the toilet seat ring 215 should be up, leaving the bare toilet rim 205 of the toilet bowl 210 exposed.

Next, at step 1220, a person (e.g., the user) places the assembled sample collection device 100, in this case the collection bowl 110 coupled with the sample cup 120 (as disclosed with reference to the above figures), on the bare toilet rim 205 of the toilet bowl 210.

Next, at step 1225, a person (e.g., the user) replaces the toilet seat ring 215 down over the assembled sample collection device 100. In another embodiment, the user can leave the toilet seat ring 215 up and simply sit on the sample collection device 100.

Next, at step 1230, the user sits down on the toilet seat ring 215 of the toilet 201 causing significant pressure vertically on the collector seat rim 490 of the sample collection device 100 from the underside of the toilet seat ring 215 of the toilet 201. The compressive forces created when the user is sitting on the toilet seat ring 215 of the toilet 201 advantageously keep the sample collection device 100 firmly in place, disallowing lateral movement, during use thereby making the user more comfortable with the experience.

Next, at step 1235, the user urinates into the sample collection device 100.

In some embodiments, the user can urinate only a small amount (approximately the amount desired for the sample) into the sample collection device 100. In other embodiments, particularly those in which the user has incontinence or weak bladder control, the user empties the entire contents of their bladder into the sample collection device 100. In some embodiments, the sample collection device 100 can be sized to accept a volume corresponding to a full human bladder. In other embodiments, the sample collection device 100 can be sized to accept, for example, twice or three time the volume of a full human bladder.

Next, at step 1240, the user stands up from the toilet 201 and lifts the toilet seat ring 215 of the toilet 201.

Next, at step 1245, a person (e.g., the user) empties the excess urine from the sample collection device 100. A person (e.g., the user) slides the entire sample collection device 100 forward (e.g., toward the user) until the back portion slips into the toilet bowl 210 and the right rear notch 795 and left rear notch 796 fit over the corners formed by the toilet rim 205; pivot the entire sample collection device 100 on the right rear notch 795 and left rear notch 796 until the sample collection device 100 is resting generally vertically (e.g., about 70°, about 80°, about 90°) on the right rear notch 795 and left rear notch 796; allow the excess urine to flow out the back of the device. The right rear notch 795 and left rear notch 796 allow the process to be dramatically simplified in that the user need not actually pick up the device to use it fully, therefore it is particularly well suited for individuals with motor disabilities or weakness who would be unable to carefully lift the sample collection device 100.

Next, at step 1250, a person (e.g., the user) removes the sample cup 120 from the collection bowl 110.

Next, at step 1255, a person (e.g., the user) places a cap on the sample cup 120, thereby producing a finished urine sample ready to be surrendered to a health care professional.

Next, at step 1260, a person (e.g., the user) discards the used sample collection device 100.

Method of Use for Kidney Stone Collection

Figure 13:
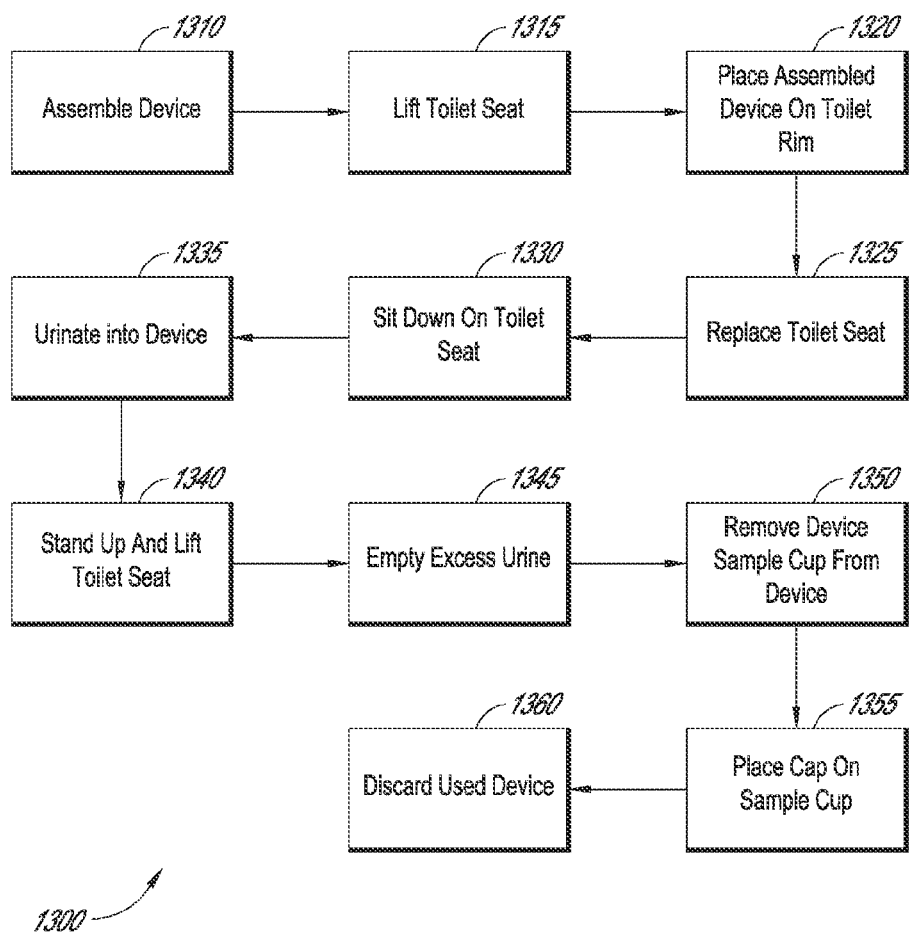
FIG. 13 is a flow chart of one embodiment of a method for collecting kidney stones using a system for collecting samples of human waste products.

FIG. 13 illustrates a method of collecting kidney stones using the sample collection device 100 disclosed herein 1300.

First, at step 1310, a person (e.g., user, medical assistant) assembles the sample collection device 100. Generally, for the collection of kidney stones the user will use the collection basket 130 and screen 140, sample cup 120 and the collection bowl 110. It will usually be unnecessary to use the sample spatula 1100 for the collection of kidney stones.

Next, at step 1315, a person (e.g., the user) lifts the toilet seat ring 215 of FIG. 2 of the toilet 201 of FIG. 2. Both the lid and the toilet seat ring 215 should be up, leaving the bare toilet rim 205 of the toilet bowl 210 exposed.

Next, at step 1320, a person (e.g., the user) places the assembled sample collection device 100, in this case the collection bowl 110 coupled with the sample cup 120 which includes the collection basket 130 and screen 140 (as disclosed with reference to the above figures), on the bare toilet rim 205 of the toilet bowl 210.

Next, at step 1325, a person (e.g., the user) replaces the toilet seat ring 215 down over the assembled sample collection device 100. In another embodiment, the user can leave the toilet seat ring 215 up and simply sit on the sample collection device 100.

Next, at step 1330, the user sits down on the toilet seat ring 215 of the toilet 201 causing significant pressure vertically on the collector seat rim 490 of the sample collection device 100 from the underside of the toilet seat ring 215 of the toilet 201. The compressive forces created when the user is sitting on the toilet seat ring 215 of the toilet 201 advantageously keep the sample collection device 100 firmly in place during use thereby making the user more comfortable with the experience.

Next, at step 1335, the user urinates into the sample collection device 100. When collecting kidney stones, the user can advantageously urinate the entirety of their bladder into the sample collection device 100 to obtain all kidney stones and fragments of kidney stones possible. Were the user to urinate only a portion of their bladder into the sample collection device 100, it is possible if not likely that stones would remain in the bladder or kidneys.

Next, at step 1340, the user stands up from the toilet 201 and lifts the toilet seat ring 215 of the toilet 201.

Next, at step 1345, a person (e.g., the user) carefully empties the excess urine from the sample collection device 100 to advantageously keep the kidney stones in the collection basket 130. A person (e.g., the user) slides the entire sample collection device 100 forward until the back portion slips into the toilet bowl 210 until the right rear notch 795 and left rear notch 796 fit over the corners formed by the toilet rim 205; pivot the entire sample collection device 100 on the right rear notch 795 and left rear notch 796 until the sample collection device 100 is resting generally vertically (e.g., about 70°, about 80°, about 90°) on the right rear notch 795 and left rear notch 796; allow the excess urine to flow out the back of the device. The right rear notch 795 and left rear notch 796 allow the process to be dramatically simplified in that the user need not actually pick up the device to use it fully, therefore it is particularly well suited for individuals with motor disabilities or weakness who would be unable to carefully lift the sample collection device 100.

Next, at step 1350, a person (e.g., the user) removes the sample cup 120 from the collection bowl 110.

Next, at step 1355, a person (e.g., the user) places a cap on the sample cup 120, thereby producing a finished urine sample, as well as any kidney stones that may have been collected, ready to be surrendered to a health care professional.

Next, at step 1360, a person (e.g., the user) discards the used sample collection device 100.

Method of Use for Stool Samples

Figure 14:
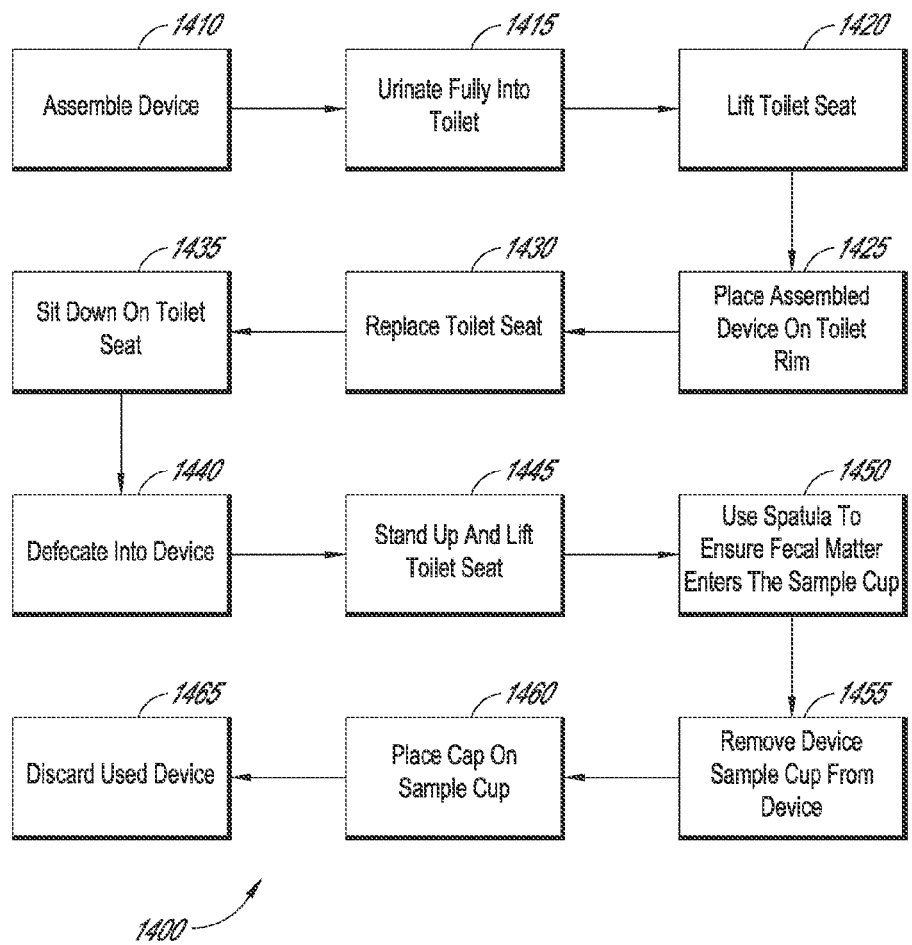
FIG. 14 is a flow chart of one embodiment of a method for collecting a stool sample using a system for collecting samples of human waste products.

FIG. 14 illustrates a method of collecting a stool sample using the sample collection device 100 disclosed herein 1400.

First, at step 1410, a person (e.g., user, medical assistant) assembles the sample collection device 100. Generally, for a stool sample only the sample cup 120 is necessary along with the collection bowl 110 and the sample spatula 1100. Neither the collection basket 130 not the screen 140 is necessary for a simple stool sample collection.

Next, at step 1415, the user urinates as fully as possible without emptying their bowels. When collecting a stool sample it can be undesirable to contaminate the stools with urine. Therefore, prior to taking a stool sample using the sample collection device 100, it is advantageous that the user should empty their bladder first so as to not contaminate the sample.

Next, at step 1420, a person (e.g., the user) lifts the toilet seat ring 215 of FIG. 2 of the toilet 201 of FIG. 2. Both the lid and the toilet seat ring 215 should be up, leaving the bare toilet rim 205 of the toilet bowl 210 exposed.

Next, at step 1425, a person (e.g., the user) places the assembled sample collection device 100, in this case the collection bowl 110 coupled with the sample cup 120 (as disclosed with reference to the above figures), on the bare toilet rim 205 of the toilet bowl 210.

Next, at step 1430, a person (e.g., the user) replaces the toilet seat ring 215 down over the assembled sample collection device 100. In another embodiment, the user can leave the toilet seat ring 215 up and simply sit on the sample collection device 100.

Next, at step 1435, the user sits down on the toilet seat ring 215 of the toilet 201 causing significant pressure vertically on the collector seat rim 490 of the sample collection device 100 from the underside of the toilet seat ring 215 of the toilet 201. The compressive forces created when the user is sitting on the toilet seat ring 215 of the toilet 201 advantageously keep the sample collection device 100 firmly in place during use thereby making the user more comfortable with the experience.

Next, at step 1440, the user defecates into the sample collection device 100.

In some embodiments, the user can defecate only a small amount (approximately the amount desired for the sample) into the sample collection device 100. In other embodiments, particularly those in which the user has weak bowel control, the user empties the entire contents of their bowls into the sample collection device 100.

Next, at step 1445, the user stands up from the toilet 201 and lifts the toilet seat ring 215 of the toilet 201.

Next, at step 1450, a person (e.g., the user) uses the sample spatula 1100 to ensure that a stool sample is in the sample cup 120.

Next, at step 1455, a person (e.g., the user) removes the sample cup 120 from the collection bowl 110.

Next, at step 1460, a person (e.g., the user) places a cap on the sample cup 120, thereby producing a finished stool sample ready to be surrendered to a health care professional.

Next, at step 1465, a person (e.g., the user) discards the used sample collection device 100 and the used sample spatula 1100.

Additional Views of the Sample Collection Device

Figure 15:
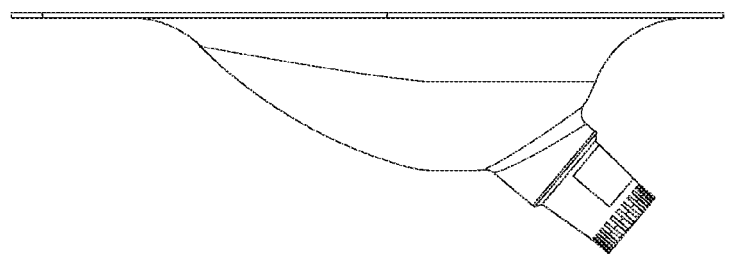
FIG. 15 is a left-side schematic view of one embodiment of a system for collecting samples of human waste products.

FIG. 15 is a left-side schematic view of one embodiment of a system for collecting samples of human waste products.

Figure 16:
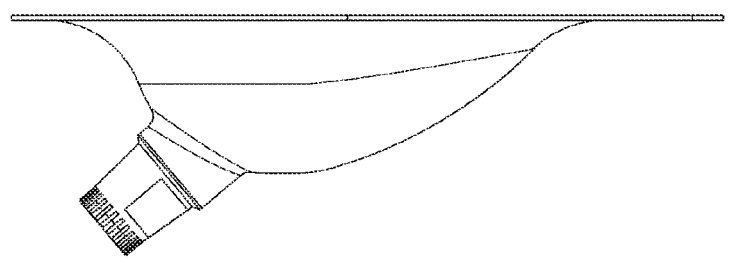
FIG. 16 is a right-side schematic view of the system for collecting samples of human waste products of FIG. 15.

FIG. 16 is a right-side schematic view of one embodiment of a system for collecting samples of human waste products.

Figure 17:
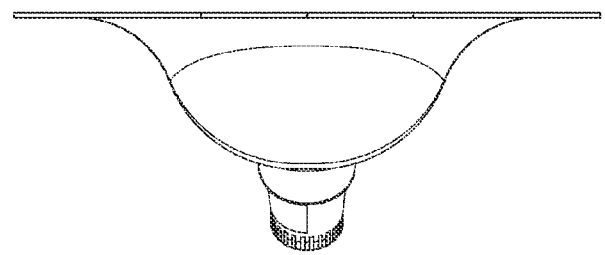
FIG. 17 is a front schematic view of the system for collecting samples of human waste products of FIG. 15.

FIG. 17 is a front schematic view of one embodiment of a system for collecting samples of human waste products.

Figure 18:
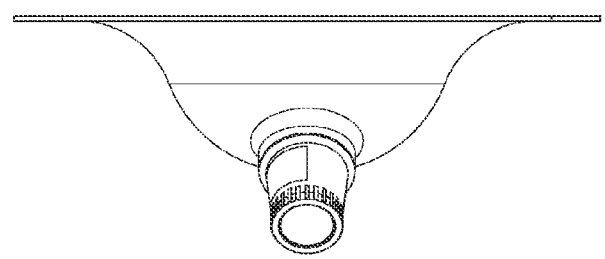
FIG. 18 is a rear schematic view of the system for collecting samples of human waste products of FIG. 15.

FIG. 18 is a rear schematic view of one embodiment of a system for collecting samples of human waste products.

Figure 19:
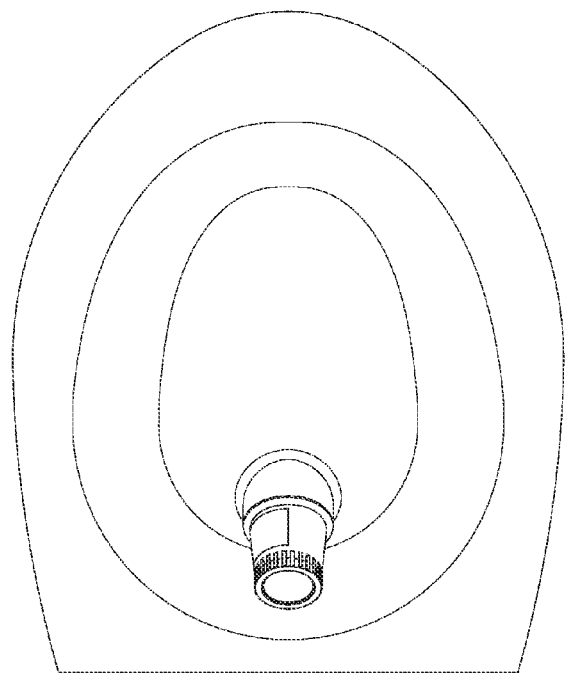
FIG. 19 is a bottom schematic view of the system for collecting samples of human waste products of FIG. 15.

FIG. 19 is a bottom schematic view of one embodiment of a system for collecting samples of human waste products.

Figure 20:
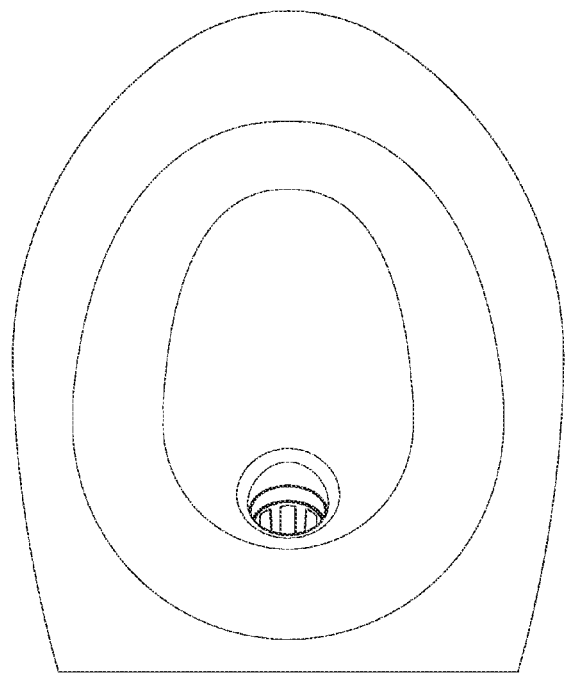
FIG. 20 is a top schematic view of the system for collecting samples of human waste products of FIG. 15.

FIG. 20 is a top schematic view of one embodiment of a system for collecting samples of human waste products.

Figure 21:
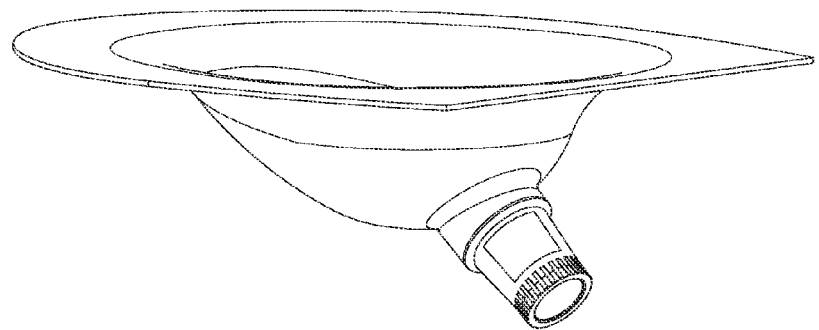
FIG. 21 is a top-biased, left-side, rear three-quarter schematic view of the system for collecting samples of human waste products of FIG. 15.

FIG. 21 is a top-biased, left-side, rear three-quarter schematic view of one embodiment of a system for collecting samples of human waste products.

Figure 22:
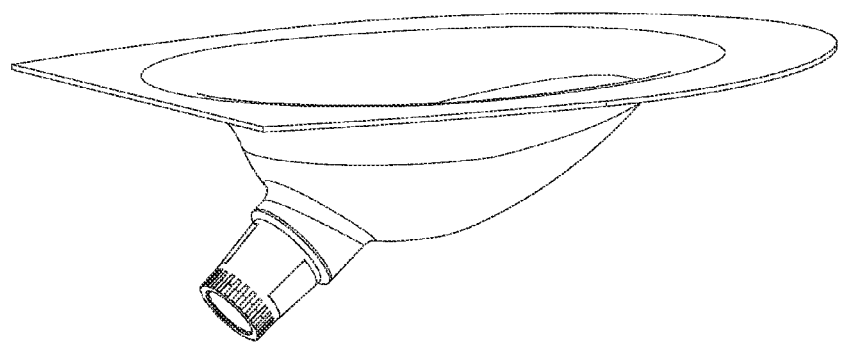
FIG. 22 is a top-biased, right-side, rear three-quarter schematic view of the system for collecting samples of human waste products of FIG. 15.

FIG. 22 is a top-biased, right-side, rear three-quarter schematic view of one embodiment of a system for collecting samples of human waste products.

Figure 23:
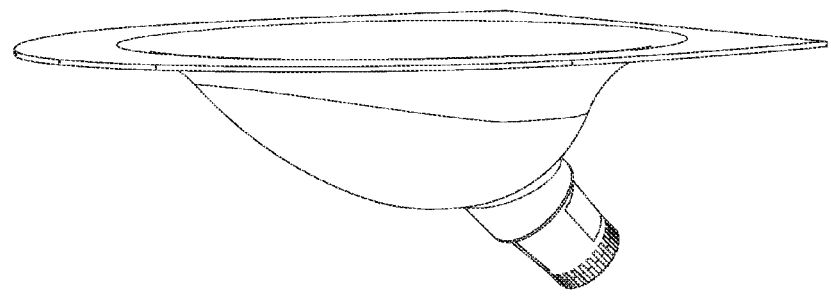
FIG. 23 is a top-biased, left-side, front three-quarter schematic view of the system for collecting samples of human waste products of FIG. 15.

FIG. 23 is a top-biased, left-side, front three-quarter schematic view of one embodiment of a system for collecting samples of human waste products.

Figure 24:
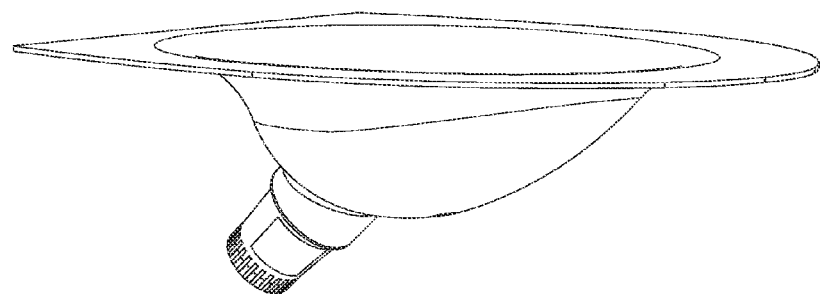
FIG. 24 is a top-biased, right-side, front three-quarter schematic view of the system for collecting samples of human waste products of FIG. 15.

FIG. 24 is a top-biased, right-side, front three-quarter schematic view of one embodiment of a system for collecting samples of human waste products.

Figure 25:
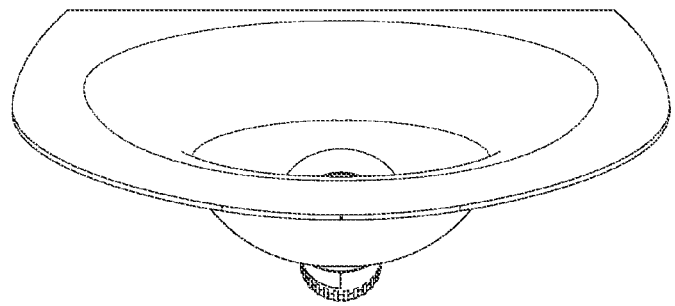
FIGS. 25 and 26 are top-biased, front schematic views of the system for collecting samples of human waste products of FIG. 15.
Figure 26:
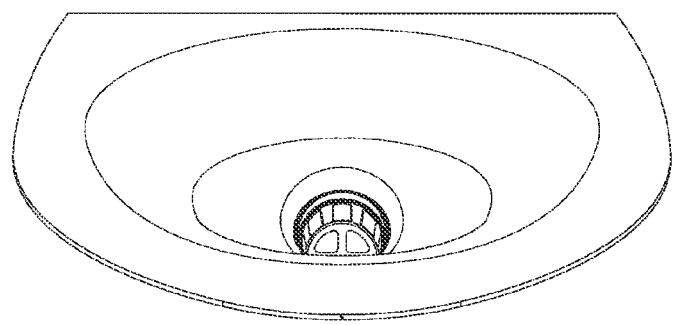

FIGS. 25 and 26 are top-biased, front schematic views of one embodiment of a system for collecting samples of human waste products.

Figure 27:
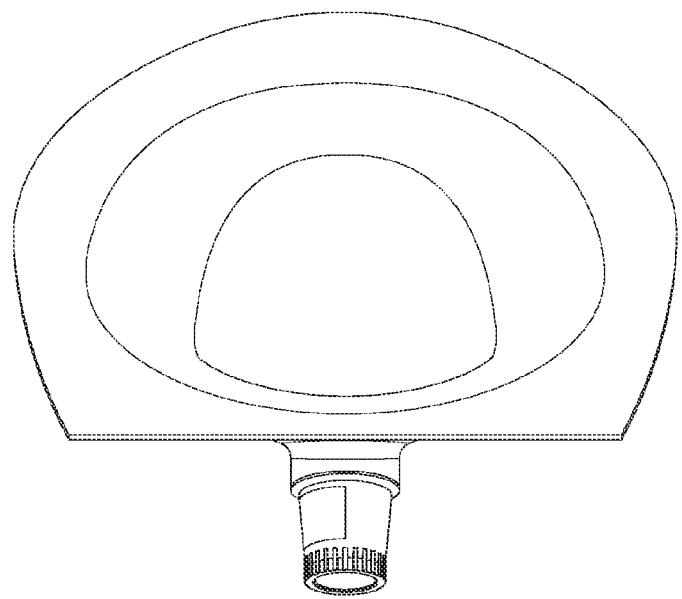
FIG. 27 is a top-biased, rear schematic view of the system for collecting samples of human waste products of FIG. 15.
Figure 28:
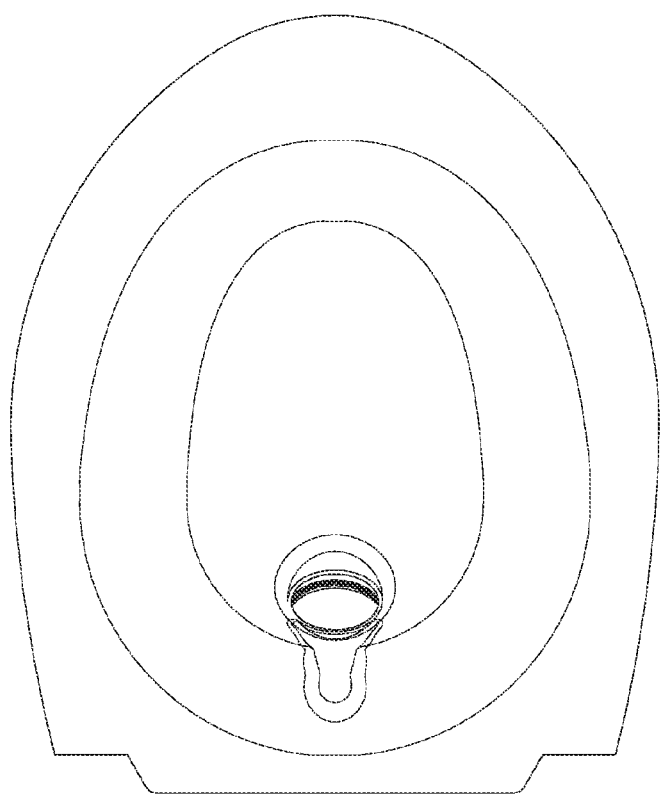
FIG. 28 is a top schematic view of another embodiment of a device for collecting samples of human waste products.
Figure 29:
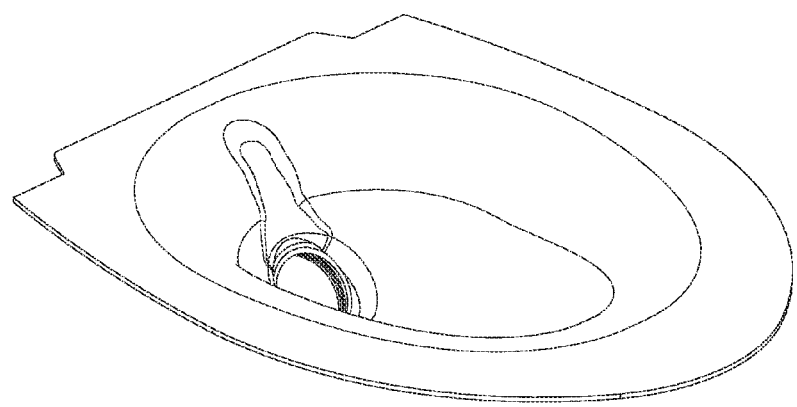
FIG. 29 is a top-biased, right-side, front three-quarter schematic view of the device for collecting samples of human waste products of FIG. 28.
Figure 30:
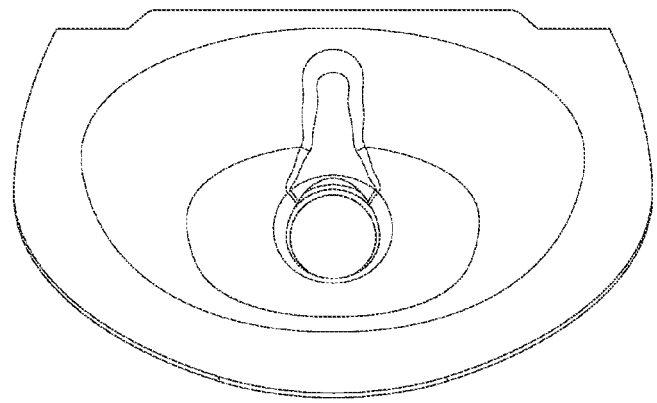
FIG. 30 is a top-biased, front schematic view of the device for collecting samples of human waste products of FIG. 28.
Figure 31:
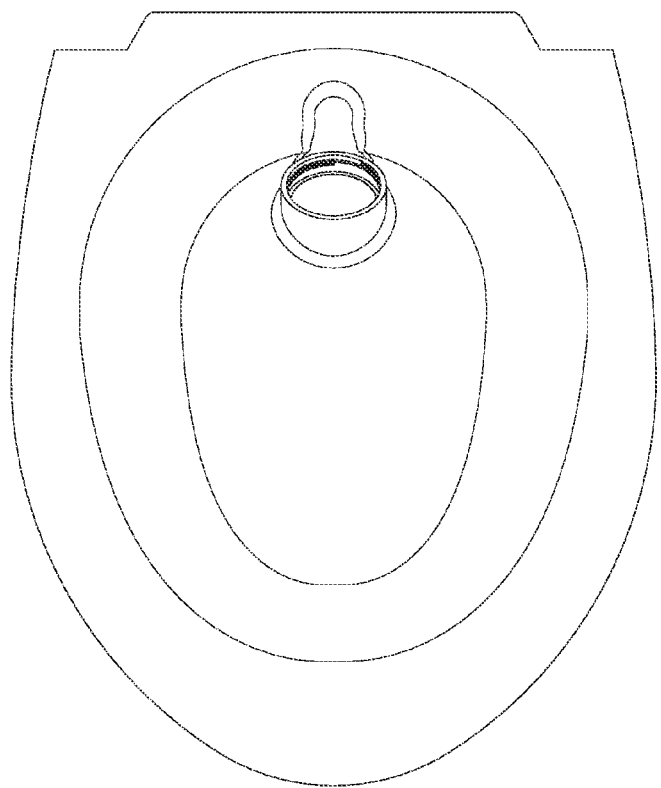
FIG. 31 is a bottom schematic view of the device for collecting samples of human waste products of FIG. 28.
Figure 32:
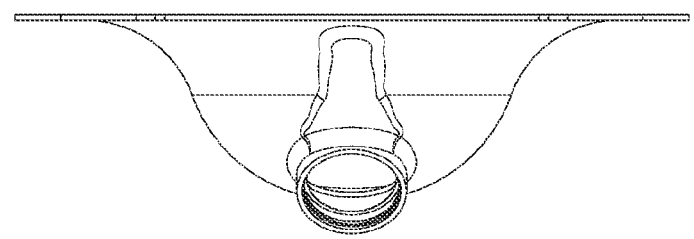
FIG. 32 is a rear schematic view of the device for collecting samples of human waste products of FIG. 28.
Figure 33:
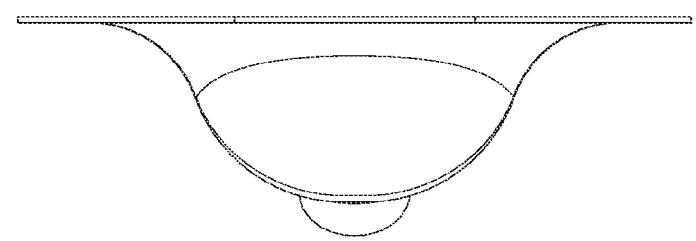
FIG. 33 is a front schematic view of the device for collecting samples of human waste products of FIG. 28.
Figure 34:
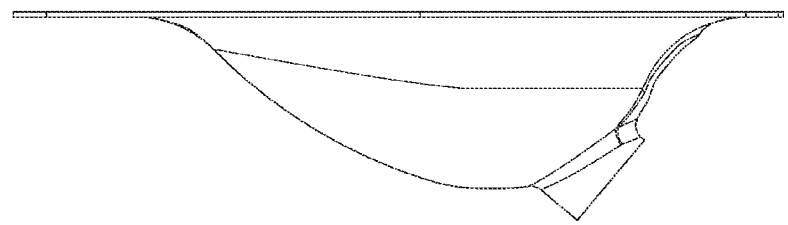
FIG. 34 is a left schematic view of the device for collecting samples of human waste products of FIG. 28.
Figure 35:
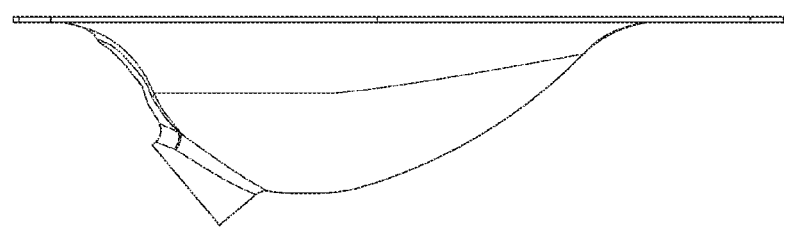
FIG. 35 is a right schematic view of the device for collecting samples of human waste products of FIG. 28.

FIG. 27 is a top-biased, rear schematic view of one embodiment of a system for collecting samples of human waste products.

FIGS. 28-35 show views of another embodiment of a sample collection device, without a sample cup, collection basket or screen (e.g., without the sample cup 120, collection basket 130, or screen 140).

Of course, the foregoing description is of certain features, aspects and advantages of the present invention, to which various changes and modifications can be made without departing from the spirit and scope of the present invention. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of the specific features and aspects between and among the different embodiments may be made and still fall within the scope of the invention. Accordingly, it should be understood that various features and aspects of the disclosed embodiments can be combined with or substituted for one another in order to form varying modes of the discussed devices, systems and methods (e.g., by excluding features or steps from certain embodiments, or adding features or steps from one embodiment of a system or method to another embodiment of a system or method).

What is claimed is:

1. A sample collection system for urine, stool or kidney stone samples, comprising:

a monolithic sample collection body having one continuous piece of material with a circumferential rim having a shape corresponding to a shape of a toilet rim configured to contact the circumferential rim when the sample collection body is placed on the toilet, and a collection bowl that extends downwardly from the circumferential rim, the sample collection body configured for placement on the toilet such that the circumferential rim is positioned on the toilet rim and the collection bowl extends into a bowl portion of the toilet, the collection body further defining a collector port at a bottom of the collection bowl that extends to a bottom opening of the collection bowl; and a sample cup releasably coupleable to the collector port of the sample collection body such that a collection volume of the sample cup is in communication with the collection bowl, wherein the sample collection body is configured to receive a urine, stool or kidney stone sample from a user and direct it to the collection volume in the sample cup via the collection bowl.

2. The system of claim 1, further comprising a collection basket removably insertable in the sample cup, the collection basket being shorter than the sample cup and comprising a screen configured to allow a liquid to flow therethrough and to inhibit passage of solid material therethrough, wherein the collection basket is configured to collect kidney stones passed by a user in urine when providing a urine sample to the sample collection body.

3. The system of claim 1, wherein at least a portion of the sample cup abuts an outer surface of the collector port.

4. The system of claim 1, wherein at least a portion of the rim of the sample collection body is planar.

5. The system of claim 1, wherein a distal portion of the rim of the sample collection body is configured to extend into the toilet bowl when a user lifts the proximal end of the rim of the sample collection body, thereby allowing the dispensation of overflow of the sample into the toilet while inhibiting emptying of the sample collected in the sample cup.

6. The system of claim 1, wherein the rim of the sample collection body is configured to be interposed between the rim of the toilet and a toilet seat of the toilet, such that when in use the rim of the sample collection body is clamped between the rim of the toilet and the toilet seat.

7. The system of claim 1, wherein the collector port extends along a central axis that defines an acute angle with a plane defined by the rim of the sample collection body, such that the sample cup extends at an angle relative to said plane defined by the rim of the sample collection body when coupled to the collector port, a bottom end of the sample cup extending toward a distal end of the sample collection body.

8. The system of claim 1, further comprising a tab on a front end of the sample collection body that does not contact the toilet when the sample collection body is disposed on the toilet, the tab configured to be grasped by the user to lift the front end of the sample collection body relative to a rear end of the sample collection body to dispose of an overflow of the sample via the rear end of the sample collection body into the toilet.

9. The system of claim 7, wherein the angle defined by the central axis is 40 degrees.

10. The system of claim 1, wherein the sample collection body is configured such that only the rim of the sample collection body contacts a surface of the toilet.

11. The system of claim 1, wherein the sample collection body is made of a polymer material.

12. A sample collection system for urine, stool or kidney stone samples, comprising:

a semi-rigid sample collection body having a circumferential rim with a shape corresponding to a shape of a toilet rim configured to contact the circumferential rim when the sample collection body is placed on the toilet, and a collection bowl that extends downwardly from the circumferential rim and defines one or more drainage troughs, the sample collection body configured for placement on the toilet such that the circumferential rim is interposed between the toilet rim and a toilet seat when in use, and such that the collection bowl extends into a bowl portion of the toilet, the collection body further defining a collector port at a bottom of the collection bowl and in communication with the one or more drainage troughs, the collector port comprising a port coupling member; and a sample cup releasably coupleable to the collector port of the sample collection body such that a collection volume of the sample cup is in communication with the collection bowl, the sample cup having a cup coupling member configured to releasably couple to the port coupling member, at least a portion of the sample cup abutting an outer surface of the collector port, wherein the sample collection body is configured to receive a urine, stool or kidney stone sample from a user and direct it to the collection volume in the sample cup via the collection bowl, and wherein only the rim of the sample collection body contacts a surface of the toilet.

13. The system of claim 12, further comprising a collection basket removably insertable in the sample cup, the collection basket being shorter than the sample cup and comprising a screen configured to allow a liquid to flow therethrough and to inhibit passage of solid material therethrough, wherein the collection basket is configured to collect kidney stones passed by a user in urine when providing a urine sample to the sample collection body.

14. The system of claim 12, wherein at least a portion of the rim of the sample collection body is U-shaped.

15. The system of claim 12, wherein a distal portion of the rim of the sample collection body is configured to extend into the toilet bowl when a user lifts the proximal end of the rim of the sample collection body, thereby allowing the dispensation of overflow of the sample into the toilet while inhibiting emptying of the sample collected in the sample cup.

16. The system of claim 12, wherein the collector port extends along a central axis that defines an acute angle with a plane defined by the rim of the sample collection body, such that the sample cup extends at an angle relative to said plane defined by the rim of the sample collection body when coupled to the collector port, a bottom end of the sample cup extending toward a distal end of the sample collection body.

17. The system of claim 16, wherein the angle is 40 degrees.

18. The system of claim 12, wherein the sample collection body is made of a polymer material.

19. A kit for use within an interior of a toilet bowl to collect a urine, stool or kidney stone sample, comprising:

a monolithic sample collection body having one continuous piece of material with a circumferential rim having a shape corresponding to a shape of a toilet rim configured to contact the circumferential rim when the sample collection body is placed on the toilet and a curved collection bowl that extends downwardly from the circumferential rim to a collector port, the collector port extending at an angle relative to a plane defined by the rim;

a sample cup for releasably coupleable to the collector port of the sample collection body to place a collection volume of the sample cup in communication with the collection bowl, at least a portion of the sample cup abutting an outer surface of the collector port;

a collection basket removably insertable in the sample cup, the collection basket comprising a screen configured to allow a liquid to flow therethrough and inhibit passage of solid material therethrough.

20. The kit of claim 19, further comprising a spatula for facilitating placement of a solid sample in the sample cup.

* * * * *